United States Patent
Boehm

(10) Patent No.: US 11,679,214 B2
(45) Date of Patent: Jun. 20, 2023

(54) ENERGY TRANSFER CIRCUIT

(71) Applicant: ResMed Pty Ltd, Bella Vista (AU)

(72) Inventor: David Paul Boehm, Sydney (AU)

(73) Assignee: ResMed Pty Ltd., Bella Vista (AU)

( * ) Notice: Subject to any disclaimer, the term of this patent is extended or adjusted under 35 U.S.C. 154(b) by 400 days.

(21) Appl. No.: 16/922,647

(22) Filed: Jul. 7, 2020

(65) Prior Publication Data

US 2021/0016033 A1    Jan. 21, 2021

Related U.S. Application Data

(60) Provisional application No. 62/874,084, filed on Jul. 15, 2019.

(51) Int. Cl.
*A61M 16/00* (2006.01)
*H02K 11/35* (2016.01)
(Continued)

(52) U.S. Cl.
CPC .... *A61M 16/0069* (2014.02); *A61M 16/0066* (2013.01); *A61M 16/022* (2017.08);
(Continued)

(58) Field of Classification Search
CPC .............. A61M 16/00; A61M 16/0066; A61M 16/0069; A61M 16/022; A61M 16/024;
(Continued)

(56) References Cited

U.S. PATENT DOCUMENTS 4,782,832 A    11/1988   Trimble et al.
4,944,310 A     7/1990   Sullivan
(Continued)

FOREIGN PATENT DOCUMENTS

WO    WO 98/004310 A1    2/1998
WO    WO 98/034665 A1    8/1998
(Continued)

OTHER PUBLICATIONS

"*Respiratory Physiology*", by John B. West, Lippincott Williams & Wilkins, 9th edition published 2012 (8 pages).

*Primary Examiner* — Joseph D. Boecker
(74) *Attorney, Agent, or Firm* — Nixon & Vanderhye, P.C.

(57) ABSTRACT

An apparatus for treating a respiratory disorder in a patient includes a power supply, a first power supply circuit coupled to the power supply, a pressure generator to generate a flow of air, a transducer to generate a flow signal representing a property of the flow of air, and motor power supply circuitry. The motor power supply circuitry includes: a motor controller to control operation of a motor in the pressure generator based on the flow signal; one or more storage elements to store energy generated by motor deceleration; an energy dissipation circuit to dissipate a portion the energy generated by the deceleration of the motor; and an energy transfer circuit to couple the one or more storage elements to the first power supply circuit and transfer the energy generated by motor deceleration and/or the energy stored by the one or more storage elements to the first power supply circuit.

32 Claims, 10 Drawing Sheets

(51) Int. Cl.
*H02K 11/26* (2016.01)
*A61M 16/06* (2006.01)
*H02K 11/33* (2016.01)
*H02K 5/128* (2006.01)
*H02K 5/173* (2006.01)
*H02K 11/215* (2016.01)

(52) U.S. Cl.
CPC ........... *A61M 16/024* (2017.08); *H02K 5/128* (2013.01); *H02K 5/173* (2013.01); *H02K 11/26* (2016.01); *H02K 11/35* (2016.01); *A61M 16/06* (2013.01); *A61M 2205/42* (2013.01); *H02K 11/215* (2016.01); *H02K 11/33* (2016.01); *H02K 2213/06* (2013.01)

(58) Field of Classification Search
CPC ........ H02K 11/26; H02K 11/33; H02K 11/35; H02K 2213/06; A62B 18/006; A62B 18/045
See application file for complete search history.

(56) References Cited

U.S. PATENT DOCUMENTS

| | | | |
|---|---|---|---|
| 6,532,959 B1 | 3/2003 | Berthon-Jones | |
| 6,581,594 B1 | 6/2003 | Drew et al. | |
| 6,603,273 B1 * | 8/2003 | Wickham | A61M 16/0066 128/204.23 |
| 7,866,944 B2 | 1/2011 | Kenyon et al. | |
| 8,636,479 B2 | 1/2014 | Kenyon et al. | |
| 8,638,014 B2 | 1/2014 | Sears et al. | |
| 8,733,349 B2 | 5/2014 | Bath et al. | |
| 2009/0044808 A1 | 2/2009 | Guney Memduh et al. | |
| 2009/0050156 A1 | 2/2009 | Ng et al. | |
| 2010/0000534 A1 | 1/2010 | Kooij et al. | |
| 2015/0120067 A1 * | 4/2015 | Wing | G05D 16/20 700/282 |
| 2016/0375209 A1 * | 12/2016 | Shadie | A61M 16/105 128/204.21 |
| 2018/0212538 A1 * | 7/2018 | Lindberg | F04D 25/06 |

FOREIGN PATENT DOCUMENTS

| | | |
|---|---|---|
| WO | WO 2000/078381 A1 | 12/2000 |
| WO | WO 2004/073778 A1 | 9/2004 |
| WO | WO 2005/063328 A1 | 7/2005 |
| WO | WO 2006/074513 A1 | 7/2006 |
| WO | WO 2006/130903 A1 | 12/2006 |
| WO | WO 2009/052560 A1 | 4/2009 |
| WO | WO 2010/135785 A1 | 12/2010 |
| WO | WO 2012/171072 A1 | 12/2012 |
| WO | WO 2013/020167 A1 | 2/2013 |
| WO | WO-2017193168 A1 * | 11/2017 ............ A61M 16/00 |

* cited by examiner

ENERGY TRANSFER CIRCUIT

1 CROSS-REFERENCE TO RELATED APPLICATIONS

This application claims priority to U.S. Provisional Application No. 62/874,084, filed Jul. 15, 2019, the entire contents of which are hereby incorporated by reference.

2 BACKGROUND OF THE TECHNOLOGY

2.1 Field of the Technology

The present technology relates to one or more of the screening, diagnosis, monitoring, treatment, prevention and amelioration of respiratory-related disorders. The present technology also relates to medical devices or apparatus, and their use. More particularly, the technology described herein relates to power management and/or transferring energy between circuits in medical devices or apparatus.

2.2 Description of the Related Art

2.2.1 Human Respiratory System and its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient $CO_2$ to meet the patient's needs. Respiratory failure may encompass some or all of the following disorders.

A patient with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

2.2.2 Therapies

Various respiratory therapies, such as Continuous Positive Airway Pressure (CPAP) therapy, Non-invasive ventilation (NIV), Invasive ventilation (IV), and High Flow Therapy (HFT) have been used to treat one or more of the above respiratory disorders.

2.2.2.1 Respiratory Pressure Therapies

Respiratory pressure therapy is the application of a supply of air to an entrance to the airways at a controlled target pressure that is nominally positive with respect to atmosphere throughout the patient's breathing cycle (in contrast to negative pressure therapies such as the tank ventilator or cuirass).

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

2.2.2.2 Flow Therapies

Not all respiratory therapies aim to deliver a prescribed therapeutic pressure. Some respiratory therapies aim to deliver a prescribed respiratory volume, by delivering an inspiratory flow rate profile over a targeted duration, possibly superimposed on a positive baseline pressure. In other cases, the interface to the patient's airways is 'open' (unsealed) and the respiratory therapy may only supplement the patient's own spontaneous breathing with a flow of conditioned or enriched gas. In one example, High Flow therapy (HFT) is the provision of a continuous, heated, humidified flow of air to an entrance to the airway through an unsealed or open patient interface at a "treatment flow rate" that is held approximately constant throughout the respiratory cycle. The treatment flow rate is nominally set to exceed the patient's peak inspiratory flow rate. HFT has been used to treat OSA, CSR, respiratory failure, COPD, and other respiratory disorders. One mechanism of action is that the high flow rate of air at the airway entrance improves ventilation efficiency by flushing, or washing out, expired $CO_2$ from the patient's anatomical deadspace. Hence, HFT is thus sometimes referred to as a deadspace therapy (DST). Other benefits may include the elevated warmth and humidification (possibly of benefit in secretion management) and the potential for modest elevation of airway pressures. As an alternative to constant flow rate, the treatment flow rate may follow a profile that varies over the respiratory cycle.

Another form of flow therapy is long-term oxygen therapy (LTOT) or supplemental oxygen therapy. Doctors may prescribe a continuous flow of oxygen enriched gas at a specified oxygen concentration (from 21%, the oxygen fraction in ambient air, to 100%) at a specified flow rate (e.g., 1 litre per minute (LPM), 2 LPM, 3 LPM, etc.) to be delivered to the patient's airway.

2.2.2.3 Supplementary Oxygen

For certain patients, oxygen therapy may be combined with a respiratory pressure therapy or HFT by adding supplementary oxygen to the pressurised flow of air. When oxygen is added to respiratory pressure therapy, this is referred to as RPT with supplementary oxygen. When oxygen is added to HFT, the resulting therapy is referred to as HFT with supplementary oxygen.

2.2.3 Respiratory Therapy Systems

These respiratory therapies may be provided by a respiratory therapy system or device. Such systems and devices may also be used to screen, diagnose, or monitor a condition without treating it.

A respiratory therapy system may comprise a Respiratory Pressure Therapy Device (RPT device), an air circuit, a humidifier, a patient interface, an oxygen source, and data management.

Another form of therapy system is a mandibular repositioning device.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 $cmH_2O$ relative to ambient pressure. For other forms of therapy, such as the delivery of oxygen, the patient interface may not include a seal sufficient to facilitate delivery to the airways of a supply of gas at a positive pressure of about 10 $cmH_2O$. For flow therapies such as nasal HFT, the patient interface is configured to insufflate the nares but specifically to avoid a complete seal. One example of such a patient interface is a nasal cannula.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressure-controlled (for respiratory pressure therapies) or flow-controlled (for flow therapies such as HFT). Thus RPT devices may also act as flow therapy devices. Examples of RPT devices include a CPAP device and a ventilator.

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO 3744 in CPAP mode at 10 cmH$_2$O).

| RPT Device name | A-weighted sound pressure level dB(A) | Year (approx.) |
| --- | --- | --- |
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4i ™ Humidifier | 31.1 | 2005 |
| S9 AutoSet ™ | 26.5 | 2010 |
| S9 AutoSet ™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

2.2.3.2 Air Circuit

An air circuit is a conduit or a tube constructed and arranged to allow, in use, a flow of air to travel between two components of a respiratory therapy system such as the RPT device and the patient interface. In some cases, there may be separate limbs of the air circuit for inhalation and exhalation. In other cases, a single limb air circuit is used for both inhalation and exhalation.

2.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air. Humidifiers therefore often have the capacity to heat the flow of air was well as humidifying it.

A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small. A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore medical humidifiers may have more stringent safety constraints than industrial humidifiers While a number of medical humidifiers are known, they can suffer from one or more shortcomings. Some medical humidifiers may provide inadequate humidification, some are difficult or inconvenient to use by patients.

BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

A first aspect of the present technology relates to apparatus used in the screening, diagnosis, monitoring, amelioration, treatment or prevention of a respiratory disorder.

Another aspect of the present technology relates to methods used in the screening, diagnosis, monitoring, amelioration, treatment or prevention of a respiratory disorder.

An aspect of certain forms of the present technology is to provide methods and/or apparatus that improve the compliance of patients with respiratory therapy.

One form of the present technology comprises an apparatus for treating a respiratory disorder in a patient, the apparatus including hardware circuitry configured to transfer energy from a motor diving circuit to another control system, where energy is needed when main power of the apparatus is turned off.

In some examples of the present technology, the other control system may include non-volatile memory and use the energy received when main power is turned off to close down the non-volatile memory.

Another aspect of one form of the present technology is directed to using a storage element in a motor power supply circuit to filter high energy peaks during high peak demands and providing another control system access to the energy stored in the storage element upon interruption of power in the other control system.

Another aspect of one form of the present technology is directed to storing energy generated by a decelerating motor in an apparatus for treating a respiratory disorder, and transferring the stored energy to another power supply circuit in the apparatus upon interruption of power from a power supply in the apparatus.

Another aspect of the present technology is directed to an apparatus for treating a respiratory disorder in a patient includes a power supply, a first power supply circuit coupled to the power supply, a pressure generator configured to generate a flow of air, a transducer configured to generate a flow signal representing a property of the flow of air, and motor power supply circuitry. The motor power supply circuitry includes: a motor controller configured to control operation of a motor in the pressure generator based on the flow signal; one or more storage elements configured to store energy generated by motor deceleration; an energy dissipation circuit configured to dissipate a portion the energy generated by the deceleration of the motor; and an energy transfer circuit configured to couple the one or more storage elements to the first power supply circuit and transfer the energy generated by motor deceleration and/or the energy stored by the one or more storage elements to the first power supply circuit.

Another aspect of the present technology is directed to an apparatus for treating a respiratory disorder in a patient, the apparatus comprising: a power supply; a pressure generator including a motor, the pressure generator configured to generate a flow of air for treating the respiratory disorder; a motor power supply circuit coupled to the power supply and the pressure generator; and a first other power supply circuit. The motor power supply circuit may include: one or more storage elements coupled to the motor and the power supply, the one or more storage elements configured to store energy supplied by the power supply, and provide stored energy to the motor during operation of the motor; and an energy transfer circuit configured to couple the one or more storage elements to the first other power supply circuit and transfer energy stored by the one or more storage elements to the first other power supply circuit, in the case of power interruption.

In examples of the preceding aspects: (a) the energy transfer circuit may be arranged to transfer power from the storage elements to the first other power supply circuit, only when a voltage difference between a voltage associated with the storage elements, and the voltage associated with the first other power supply circuit exceeds a predetermined value; (b) the motor power supply circuit operates at higher voltage than the first other power supply circuit; (c) the energy transfer circuit may be configured to transfer power to the first other power supply circuit such that the transferred power has a lower voltage than a voltage of the motor power supply circuit; (d) the motor power supply circuit may include a blocking circuit configured to block transfer of energy to the power supply; (e) the energy transfer circuit may include a first diode, a second diode and a resistor connected in series, the first diode is configured to block current flow from the first other power supply circuit to the motor power supply circuit, the second diode is configured to allow current to pass from the one or more storage elements to the first other power supply circuit when a voltage difference between a voltage on the one or more storage elements and power rail of the first other power supply circuit exceeds a predetermined value, and the resistor is configured to limit current flow from the motor power supply circuit to the first other power supply circuit, a voltage drop over the second diode ensuring a constant offset between the voltage of the first power supply circuit and that of the storage element; (f) the motor power supply circuit may further include: an energy dissipation circuit, and an active blocking diode circuit disposed on a motor power rail configured to block current flow from the motor power rail to the power supply; (g) the first other power supply circuit may include non-volatile memory; (h) the first other power supply circuit may include a cellular circuit including memory; (i) the first other power supply circuit may use the transfer energy to shut down non-volatile memory during interruption of power provided by the power supply; (j) the motor drive circuit is configured to, during controlled motor deceleration, pass the energy generated by deceleration of the motor to the one or more storage elements and/or an energy dissipation circuit; (k) further comprise one or more capacitors coupled to the power supply, the motor power supply circuit, and the first other power supply circuit; (l) the first other power supply circuit may include a cellular power circuit coupled to the power supply via a Schottky diode and the coupling circuit, the cellular power circuit may be configured to supply power to a cellular circuit including memory; (m) further comprise a transducer configured to generate a flow signal representing a property of the flow of air, and a motor controller configured to control operation of the motor based on the flow signal; (n) the one or more storage elements may be configured to store energy generated by deceleration of the motor; (o) the one or more storage elements may be configured to store energy generated by deceleration of the motor; and/or (p) the motor power supply circuit may further include an energy dissipation circuit coupled to the motor and configured to dissipate energy generate by deceleration of the motor.

Another aspect of the present technology is directed to an apparatus for providing positive pressure respiratory therapy to a patient breathing in a respiratory cycle including an inhalation portion and an exhalation portion, said apparatus comprising: a power supply; a first power supply circuit coupled to the power supply; a controllable motor-blower configured to generate a supply of air at a positive pressure relative to ambient pressure by rotating an impeller at an impeller speed, a housing holding said motor-blower, the housing comprising an inlet and a patient-connection port, the patient-connection port being structured to communicate said supply air at said positive pressure from the motor-blower to a patient interface via an air circuit in use; a sensor to monitor at least one of pressure and a flow rate of the supply of air at positive pressure and to generate a sensor output; and a motor controller coupled to the power supply and configured to adjust an operating parameter of said motor-blower in accordance with said sensor output to maintain a minimum positive pressure in said patient interface during a treatment session by causing an increase in the impeller speed during the inhalation portion of the respiratory cycle and causing a decrease in the impeller speed during the exhalation portion of the breathing cycle; and power circuitry configured and controlled to enable: storage of energy generated by deceleration of the motor-blower in one or more storage elements; dissipation of a portion the energy generated by the deceleration of the motor; transfer of energy generated by deceleration of the motor and/or the energy stored in the one or more storage elements, to the first power supply circuit; and blocking of current flowing from a motor power rail to the power supply.

In examples of the preceding aspects: (a) the first power supply circuit may include a cellular power circuit configured to supply power to a cellular circuit including memory; (b) the first power supply circuit may include non-volatile memory; (c) wherein the power circuitry includes a first diode, a second diode and a resistor connected in series between a power rail of the motor controller and the first power supply circuit, the first diode is configured to block current flow from the first power supply circuit to the motor controller, the second diode is configured to pass the energy generated by deceleration of the motor and the stored energy to the first power supply circuit when a voltage difference between a voltage on the power rail of the motor controller and a voltage of the first power supply circuit exceeds a predetermined value, and the resistor is configured to limit current flow to the first power supply circuit; and/or (d) the power circuitry may be configured to transfer the energy generated by deceleration of the motor and the stored energy to the first power supply circuit upon interruption of power provided by the power supply.

Another aspect of the present technology is directed to an apparatus for treating a respiratory disorder in a patient, the apparatus comprising: a power supply; a cellular communication power supply circuit coupled to the power supply; a pressure generator including a motor, the pressure generator configured to generate a flow of air for treating the respiratory disorder; a transducer configured to generate a flow signal representing a property of the flow of air; motor power supply circuitry coupled to the power supply and the pressure generator, the motor power supply circuitry including: a motor power rail coupling the power supply to the motor; a motor controller coupled to the motor power rail and configured to control supply of power to the motor based on the flow signal; an active blocking diode circuit disposed on the motor power rail and controlled to block transfer energy from the motor power rail to the power supply; one or more capacitors coupled to the motor power rail and configured to store energy supplied by the power supply, provide the stored energy to the motor during operation of the motor, and store energy generated by deceleration of the motor; a kinetic energy clamp circuit coupled to the motor power rail and configured to dissipate energy generated by the deceleration of the motor that is above a predetermined first voltage level; and a transfer circuit including a first diode, a second diode and resistor coupled in series between the motor power rail and the cellular communication power supply circuit, the first diode configured to block current flow from the cellular communication power supply circuit to the motor power rail, the second diode configured to allow current to pass from the one or more capacitors to the cellular communication power supply circuit when a voltage difference between a voltage on the motor power rail and a voltage of a pre-cellular module power rail exceeds a predetermined second voltage level, and the resistor configured to limit current flow from the motor power rail to the cellular communication power supply circuit.

In examples of the preceding aspects: (a) the cellular communication power supply circuit may include a power converter and memory; (b) the cellular communication power supply circuit may include non-volatile memory; and/or (c) the voltage difference between the voltage on the motor power rail and the voltage of the cellular communication power supply circuit may exceed the predetermined second voltage level upon interruption of power provided by the power supply.

Another aspect of one form of the present technology is a patient interface that is moulded or otherwise constructed with a perimeter shape which is complementary to that of an intended wearer.

An aspect of one form of the present technology is a method of manufacturing apparatus.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a portable RPT device that may be carried by a person, e.g., around the home of the person.

An aspect of one form of the present technology is a patient interface that may be washed in a home of a patient, e.g., in soapy water, without requiring specialised cleaning equipment. An aspect of one form of the present technology is a humidifier tank that may be washed in a home of a patient, e.g., in soapy water, without requiring specialised cleaning equipment.

The methods, systems, devices and apparatus described may be implemented so as to improve the functionality of a processor, such as a processor of a specific purpose computer, respiratory monitor and/or a respiratory therapy apparatus. Moreover, the described methods, systems, devices and apparatus can provide improvements in the technological field of automated management, monitoring and/or treatment of respiratory conditions, including, for example, sleep disordered breathing.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

3 BRIEF DESCRIPTION OF THE DRAWINGS

The present technology is illustrated by way of example, and not by way of limitation, in the figures of the accompanying drawings, in which like reference numerals refer to similar elements including:

3.1 Respiratory Therapy Systems

FIG. 1 shows a system including a patient 1000 wearing a patient interface 3000, in the form of nasal pillows, receiving a supply of air at positive pressure from an RPT device 4000. Air from the RPT device 4000 is conditioned in a humidifier 5000, and passes along an air circuit 4170 to the patient 1000. A bed partner 1100 is also shown. The patient is sleeping in a supine sleeping position.

FIG. 2 shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 3 shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

3.2 RPT Device

FIG. 4A shows an RPT device in accordance with one form of the present technology.

FIG. 4B is a schematic diagram of the pneumatic path of an RPT device in accordance with one form of the present technology. The directions of upstream and downstream are indicated with reference to the blower and the patient interface. The blower is defined to be upstream of the patient interface and the patient interface is defined to be downstream of the blower, regardless of the actual flow direction at any particular moment. Items which are located within the pneumatic path between the blower and the patient interface are downstream of the blower and upstream of the patient interface.

3.3 Humidifier

Figure 5A:
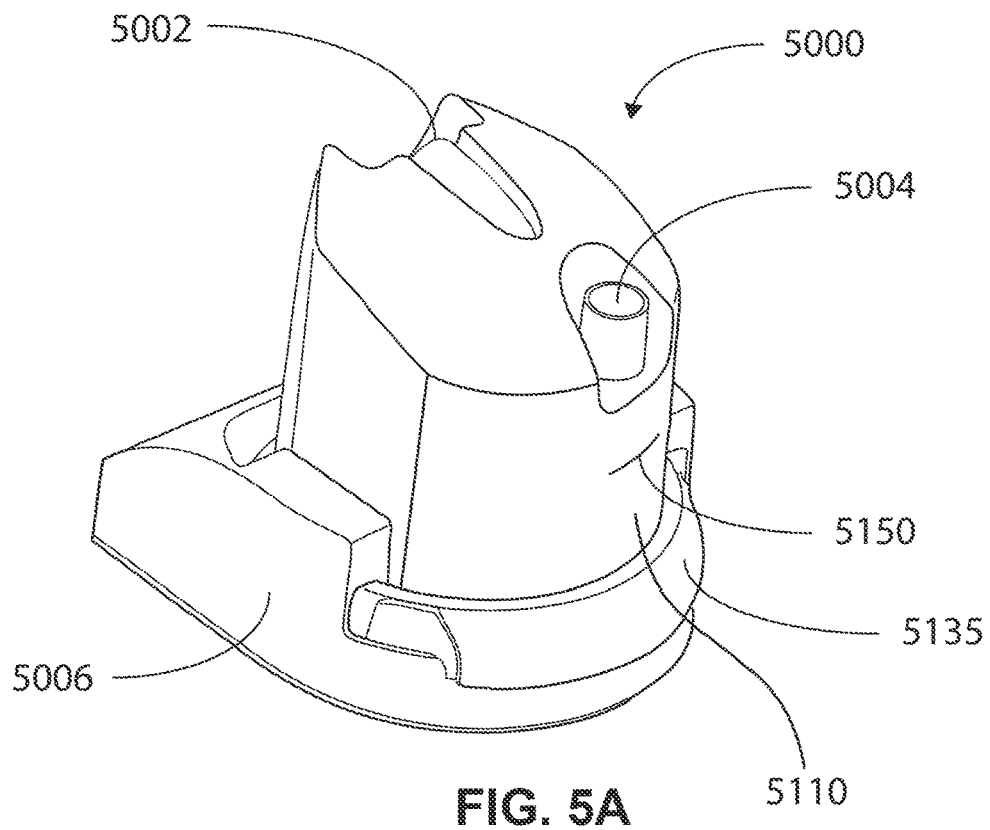

FIG. 5A shows an isometric view of a humidifier in accordance with one form of the present technology.

Figure 5B:
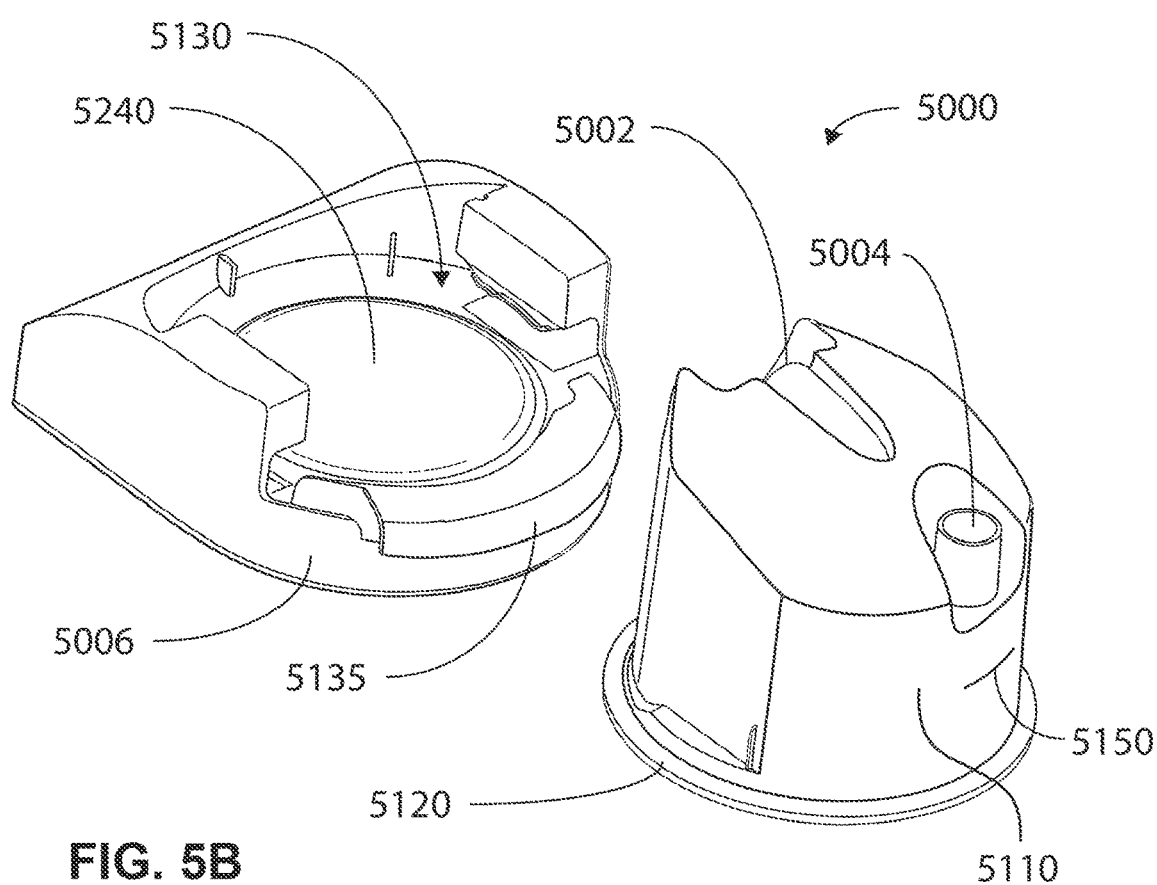

FIG. 5B shows an isometric view of a humidifier in accordance with one form of the present technology, showing a humidifier reservoir 5110 removed from the humidifier reservoir dock 5130.

4 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

4.1 Therapy

In one form, the present technology comprises a method for treating a respiratory disorder comprising applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

4.2 Respiratory Therapy Systems

In one form, the present technology comprises a respiratory therapy system for treating a respiratory disorder. The respiratory therapy system may comprise an RPT device 4000 for supplying a flow of air to the patient 1000 via an air circuit 4170 and a patient interface 3000.

4.3 Patient Interface

A non-invasive patient interface 3000 in accordance with one aspect of the present technology comprises the following functional aspects: a seal-forming structure, a plenum chamber, a positioning and stabilising structure, a vent, one form of connection port for connection to air circuit 4170, and a forehead support. In some forms a functional aspect may be provided by one or more physical components. In some forms, one physical component may provide one or more functional aspects. In use the seal-forming structure is arranged to surround an entrance to the airways of the patient so as to maintain positive pressure at the entrance(s)

to the airways of the patient 1000. The sealed patient interface 3000 is therefore suitable for delivery of positive pressure therapy.

An unsealed patient interface, in the form of a nasal cannula, includes nasal prongs which can deliver air to respective nares of the patient 1000 via respective orifices in their tips. Such nasal prongs do not generally form a seal with the inner or outer skin surface of the nares. The air to the nasal prongs may be delivered by one or more air supply lumens that are coupled with the nasal cannula. The lumens lead from the nasal cannula to a respiratory therapy device via an air circuit. The unsealed patient interface is particularly suitable for delivery of flow therapies, in which the RPT device generates the flow of air at controlled flow rates rather than controlled pressures. The "vent" at the unsealed patient interface, through which excess airflow escapes to ambient, is the passage between the end of the prongs of the cannula via the patient's nares to atmosphere.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 cmH$_2$O with respect to ambient.

The patient interface 3000 in accordance with one form of the present technology is constructed and arranged to be able to provide a supply of air at a positive pressure of at least 10 cmH$_2$O with respect to ambient.

The patient interface 3000 in accordance with one form of the present technology is constructed and arranged to be able to provide a supply of air at a positive pressure of at least 20 cmH$_2$O with respect to ambient.

4.4 RPT Device

An RPT device 4000 in accordance with one aspect of the present technology comprises mechanical, pneumatic, and/or electrical components and is configured to execute one or more algorithms, such as any of the methods, in whole or in part, described herein. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 cmH$_2$O, or at least 10cmH$_2$O, or at least 20 cmH$_2$O.

The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors 4272 and flow rate sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

4.4.1 RPT Device Mechanical & Pneumatic Components

An RPT device may comprise one or more of the following components in an integral unit. In an alternative form, one or more of the following components may be located as respective separate units.

4.4.1.1 Air Filter(s)

An RPT device in accordance with one form of the present technology may include an air filter 4110, or a plurality of air filters 4110.

In one form, an inlet air filter 4112 is located at the beginning of the pneumatic path upstream of a pressure generator 4140.

In one form, an outlet air filter 4114, for example an antibacterial filter, is located between an outlet of the pneumatic block 4020 and a patient interface 3000.

4.4.1.2 Muffler(s)

An RPT device in accordance with one form of the present technology may include a muffler 4120, or a plurality of mufflers 4120.

In one form of the present technology, an inlet muffler 4122 is located in the pneumatic path upstream of a pressure generator 4140.

In one form of the present technology, an outlet muffler 4124 is located in the pneumatic path between the pressure generator 4140 and a patient interface 3000.

4.4.1.3 Pressure Generator

In one form of the present technology, a pressure generator 4140 for producing a flow, or a supply, of air at positive pressure is a controllable blower 4142. For example the blower 4142 may include a brushless DC motor 4144 with one or more impellers. The impellers may be located in a volute. The blower may be capable of delivering a supply of air, for example at a rate of up to about 120 litres/minute, at a positive pressure in a range from about 4 cmH$_2$O to about 20 cmH$_2$O, or in other forms up to about 30 cmH$_2$O when delivering respiratory pressure therapy. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

The pressure generator 4140 is under the control of the therapy device controller 4240.

In other forms, a pressure generator 4140 may be a piston-driven pump, a pressure regulator connected to a high pressure source (e.g. compressed air reservoir), or a bellows.

4.4.1.4 Transducer(s)

Transducers may be internal of the RPT device, or external of the RPT device. External transducers may be located for example on or form part of the air circuit, e.g., the patient interface. External transducers may be in the form of non-contact sensors such as a Doppler radar movement sensor that transmit or transfer data to the RPT device.

In one form of the present technology, one or more transducers 4270 are located upstream and/or downstream of the pressure generator 4140. The one or more transducers 4270 may be constructed and arranged to generate signals representing properties of the flow of air such as a flow rate, a pressure or a temperature at that point in the pneumatic path.

In one form of the present technology, one or more transducers 4270 may be located proximate to the patient interface 3000.

In one form, a signal from a transducer 4270 may be filtered, such as by low-pass, high-pass or band-pass filtering.

4.4.1.4.1 Flow Rate Sensor

A flow rate sensor 4274 in accordance with the present technology may be based on a differential pressure transducer, for example, an SDP600 Series differential pressure transducer from SENSIRION.

In one form, a signal generated by the flow rate sensor 4274 and representing a flow rate is received by the central controller 4230.

4.4.1.4.2 Pressure Sensor

A pressure sensor 4272 in accordance with the present technology is located in fluid communication with the pneumatic path. An example of a suitable pressure sensor is a transducer from the HONEYWELL ASDX series. An alternative suitable pressure sensor is a transducer from the NPA Series from GENERAL ELECTRIC.

In one form, a signal generated by the pressure sensor 4272 is received by the central controller 4230.

4.4.1.4.3 Motor Speed Transducer

In one form of the present technology a motor speed transducer 4276 is used to determine a rotational velocity of the motor 4144 and/or the blower 4142. A motor speed signal from the motor speed transducer 4276 may be provided to the therapy device controller 4240. The motor speed transducer 4276 may, for example, be a speed sensor, such as a Hall effect sensor.

4.4.1.5 Anti-Spill Back Valve

In one form of the present technology, an anti-spill back valve 4160 is located between the humidifier 5000 and the pneumatic block 4020. The anti-spill back valve is constructed and arranged to reduce the risk that water will flow upstream from the humidifier 5000, for example to the motor 4144.

4.4.2 RPT Device Electrical Components 4.4.2.1 Power Supply

A power supply 4210 may be located internal or external of the external housing 4010 of the RPT device 4000.

In one form of the present technology, power supply 4210 provides electrical power to the RPT device 4000 only. In another form of the present technology, power supply 4210 provides electrical power to both RPT device 4000 and humidifier 5000. The power supply 4210 may be coupled to an external power source (e.g., outlet coupled to an electricity network) and/or include a battery (e.g., a rechargeable battery). The power supply 4210 may include circuitry to convert power provided by the external power source and/or a battery to power levels needed by components of the RPT device 4000. The power supply 4210 may convert an AC power to a DC power.

4.4.2.2 Input Devices

In one form of the present technology, an RPT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form, the input device 4220 may be constructed and arranged to allow a person to select a value and/or a menu option.

4.4.2.3 Central Controller

In one form of the present technology, the central controller 4230 is one or a plurality of processors suitable to control an RPT device 4000.

Suitable processors may include an x86 INTEL processor, a processor based on ARM® Cortex®-M processor from ARM Holdings such as an STM32 series microcontroller from ST MICROELECTRONIC. In certain alternative forms of the present technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS may also be suitable.

In one form of the present technology, the central controller 4230 is a dedicated electronic circuit.

In one form, the central controller 4230 is an application-specific integrated circuit. In another form, the central controller 4230 comprises discrete electronic components.

The central controller 4230 may be configured to receive input signal(s) from one or more transducers 4270, one or more input devices 4220, and the humidifier 5000.

The central controller 4230 may be configured to provide output signal(s) to one or more of an output device 4290, a therapy device controller 4240, a data communication interface 4280, and the humidifier 5000.

In some forms of the present technology, the central controller 4230 is configured to implement the one or more methodologies described herein, such as the one or more algorithms expressed as computer programs stored in a non-transitory computer readable storage medium, such as memory 4260. In some forms of the present technology, the central controller 4230 may be integrated with an RPT device 4000. However, in some forms of the present technology, some methodologies may be performed by a remotely located device. For example, the remotely located device may determine control settings for a ventilator or detect respiratory related events by analysis of stored data such as from any of the sensors described herein.

4.4.2.4 Clock

The RPT device 4000 may include a clock 4232 that is connected to the central controller 4230.

4.4.2.5 Therapy Device Controller

In one form of the present technology, therapy device controller 4240 is a therapy control module that forms part of the algorithms executed by the central controller 4230.

In one form of the present technology, therapy device controller 4240 is a dedicated motor control integrated circuit. For example, in one form a MC33035 brushless DC motor controller, manufactured by ONSEMI is used.

4.4.2.6 Protection Circuits

The one or more protection circuits 4250 in accordance with the present technology may comprise an electrical protection circuit, a temperature and/or pressure safety circuit.

4.4.2.7 Memory

In accordance with one form of the present technology the RPT device 4000 includes memory 4260, e.g., non-volatile memory. In some forms, memory 4260 may include battery powered static RAM. In some forms, memory 4260 may include volatile RAM.

Memory 4260 may be located on the PCBA 4202. Memory 4260 may be in the form of EEPROM, or NAND flash.

Additionally or alternatively, RPT device 4000 includes a removable form of memory 4260, for example a memory card made in accordance with the Secure Digital (SD) standard.

In one form of the present technology, the memory 4260 acts as a non-transitory computer readable storage medium on which is stored computer program instructions expressing the one or more methodologies described herein, such as the one or more algorithms.

4.4.2.8 Data Communication Systems

In one form of the present technology, a data communication interface 4280 is provided, and is connected to the central controller 4230. Data communication interface 4280 may be connectable to a remote external communication network 4282 and/or a local external communication network 4284. The remote external communication network 4282 may be connectable to a remote external device 4286. The local external communication network 4284 may be connectable to a local external device 4288.

In one form, data communication interface 4280 is part of the central controller 4230. In another form, data communication interface 4280 is separate from the central controller 4230, and may comprise an integrated circuit or a processor.

In one form, remote external communication network 4282 is the Internet. The data communication interface 4280 may use wired communication (e.g. via Ethernet, or optical fibre) or a wireless protocol (e.g. CDMA, GSM, LTE) to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such a remote external device 4286 may be accessible to an appropriately authorised person such as a clinician.

The local external device 4288 may be a personal computer, mobile phone, tablet or remote control.

4.4.2.9 Output Devices Including Optional Display, Alarms

An output device 4290 in accordance with the present technology may take the form of one or more of a visual, audio and haptic unit. A visual display may be a Liquid Crystal Display (LCD) or Light Emitting Diode (LED) display.

4.4.2.9.1 Display Driver

A display driver 4292 receives as an input the characters, symbols, or images intended for display on the display 4294, and converts them to commands that cause the display 4294 to display those characters, symbols, or images.

4.4.2.9.2 Display

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

4.4.2.10 Power Management

Examples of the present technology provide circuitry configured to transfer energy between different circuits. Some examples of the present technology provide systems and methods using energy storage capacitance (also known as "holdup capacitance") from one circuit to close down elements (e.g., non-volatile memory which needs energy to shut down properly) in another circuit during power interruption. As discussed in more detail below, spare energy stored in one or more capacitors of a first circuit (e.g., motor power supply circuit) can be used to close down elements in a second circuit (e.g., a cellular power supply circuit).

During operation, power provided by the electrical power supply 4210 to components of the RPT device 4000 may be interrupted. The interruption may be caused by turning off the RPT device 400, the power supply 4210 being unplugged from an external power source, failure of electricity network coupled to the power supply 4210, failure of the power supply 4210, or depletion of power stored by the power supply 4210. Other causes of the interruption may include damage to lines coupling the power supply 4210 to the external power source and/or circuitry in the RPT device 4000, a short circuit, fuse or circuit breaker operation, or overload.

Figure 1:
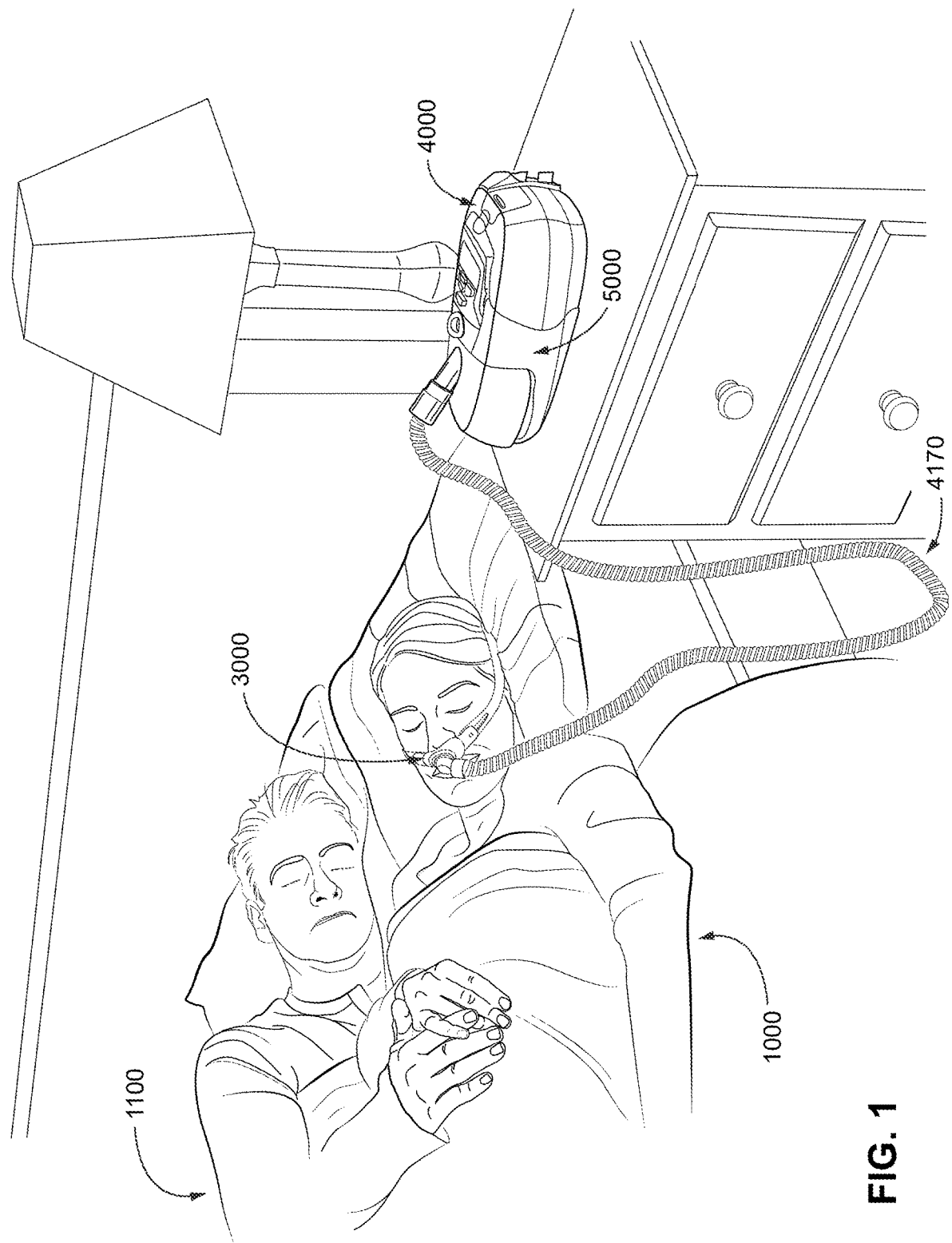
Figure 2:
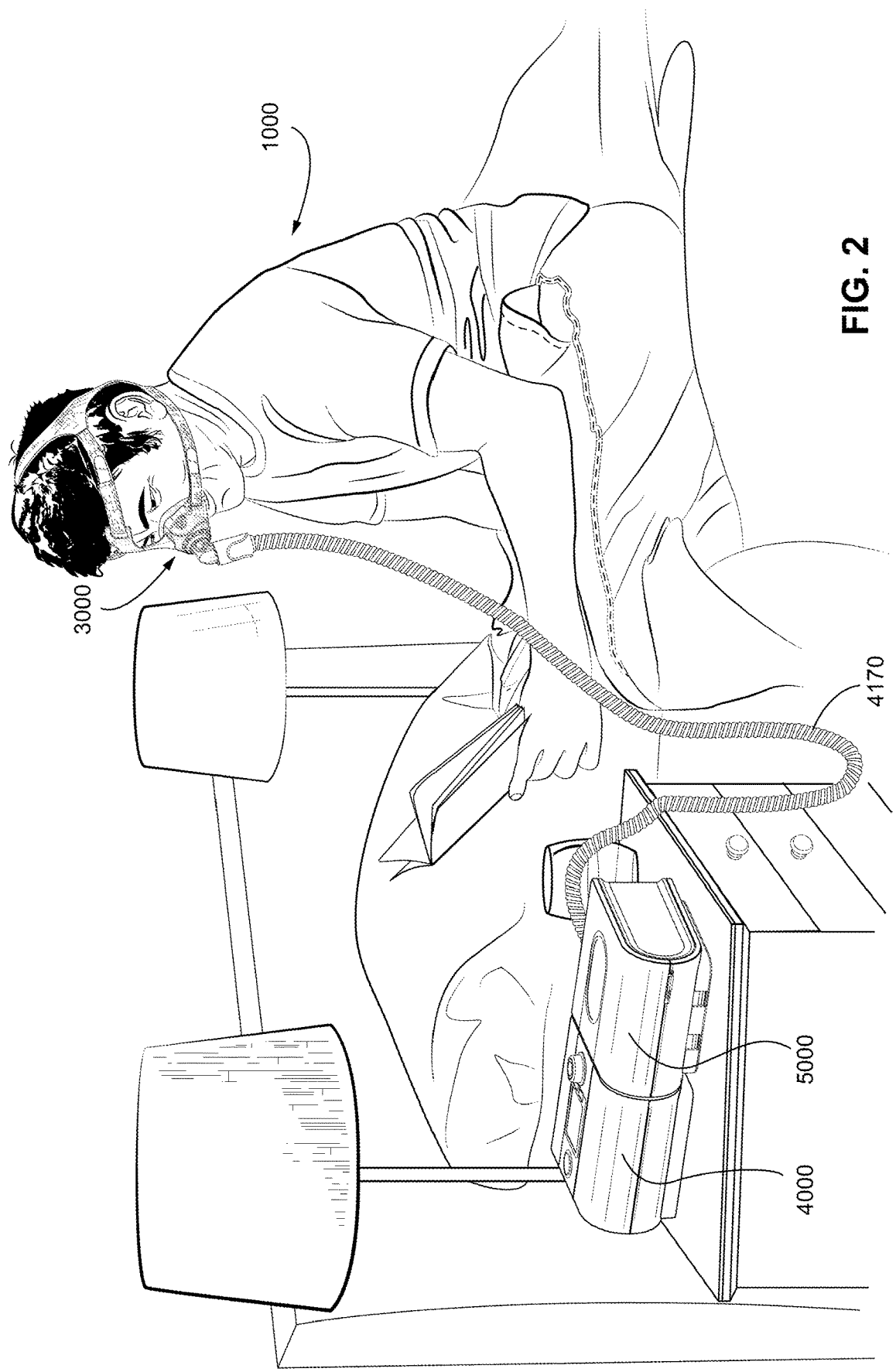
Figure 3:
Figure 4A:
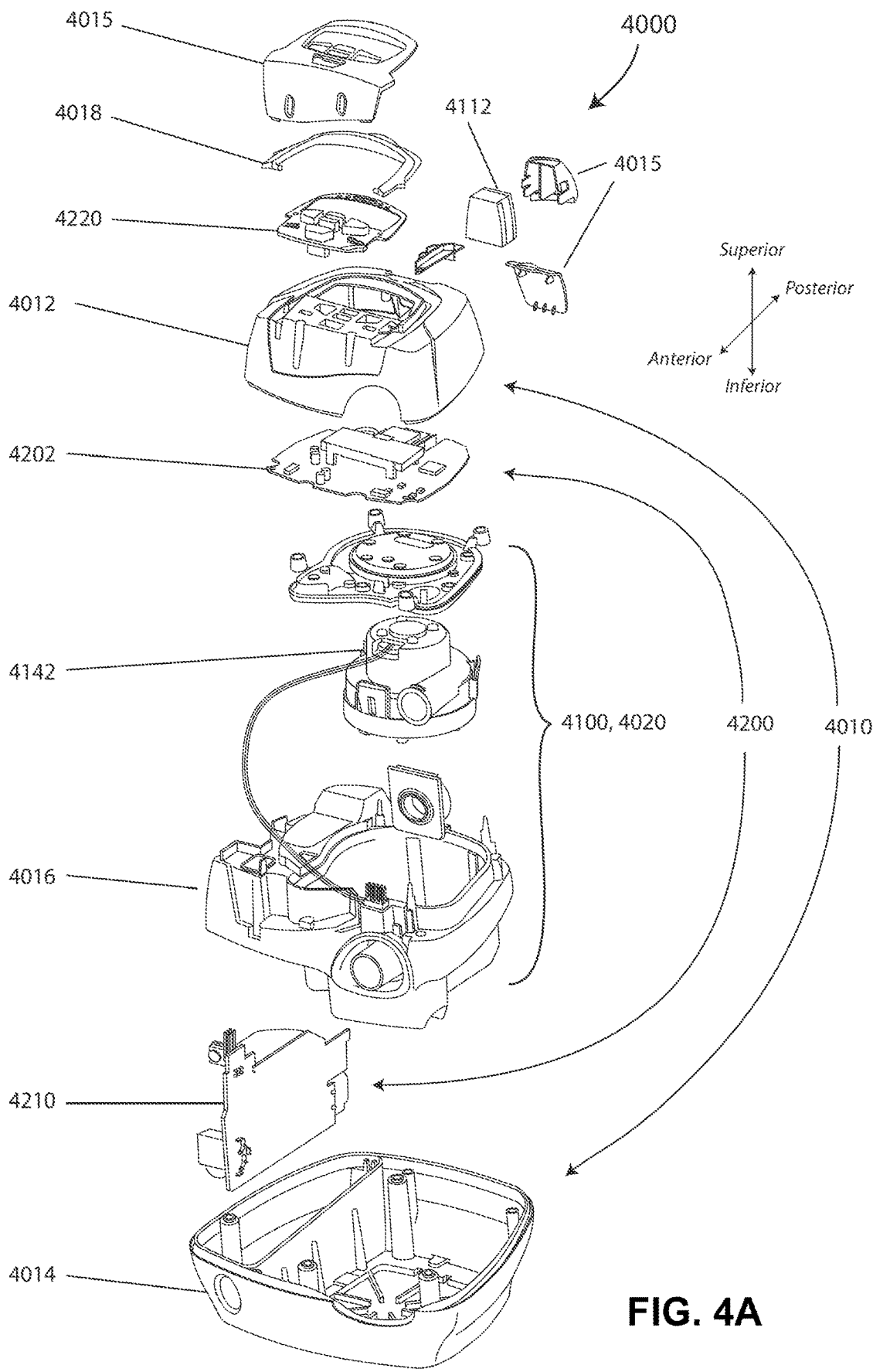
FIG. 4C is a schematic diagram of the electrical components of an RPT device in accordance with one form of the present technology.
FIG. 4D is a schematic diagram of electrical components configured to transfer energy upon power interruption in accordance with one form of the present technology.
FIG. 4E is a schematic diagram of a transfer circuit in accordance with one form of the present technology.
FIG. 4F is a schematic diagram including a circuit configured to transfer energy between power supply circuits in accordance with one form of the present technology.
FIG. 4G shows graphs of exemplary voltage levels of circuitry configured to transfer energy between power supply circuits in accordance with one form of the present technology.
Figure 4B:
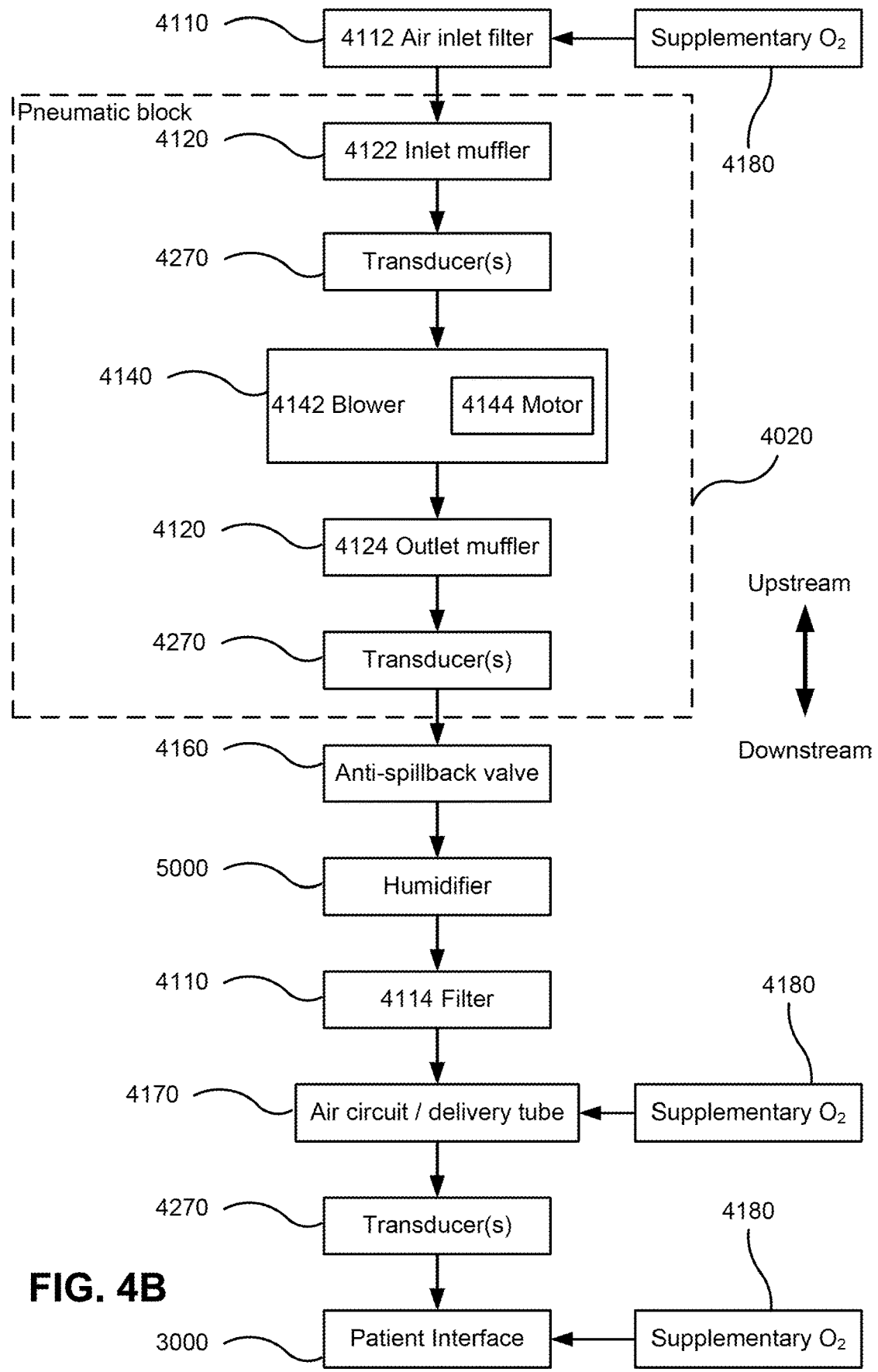
Figure 4C:
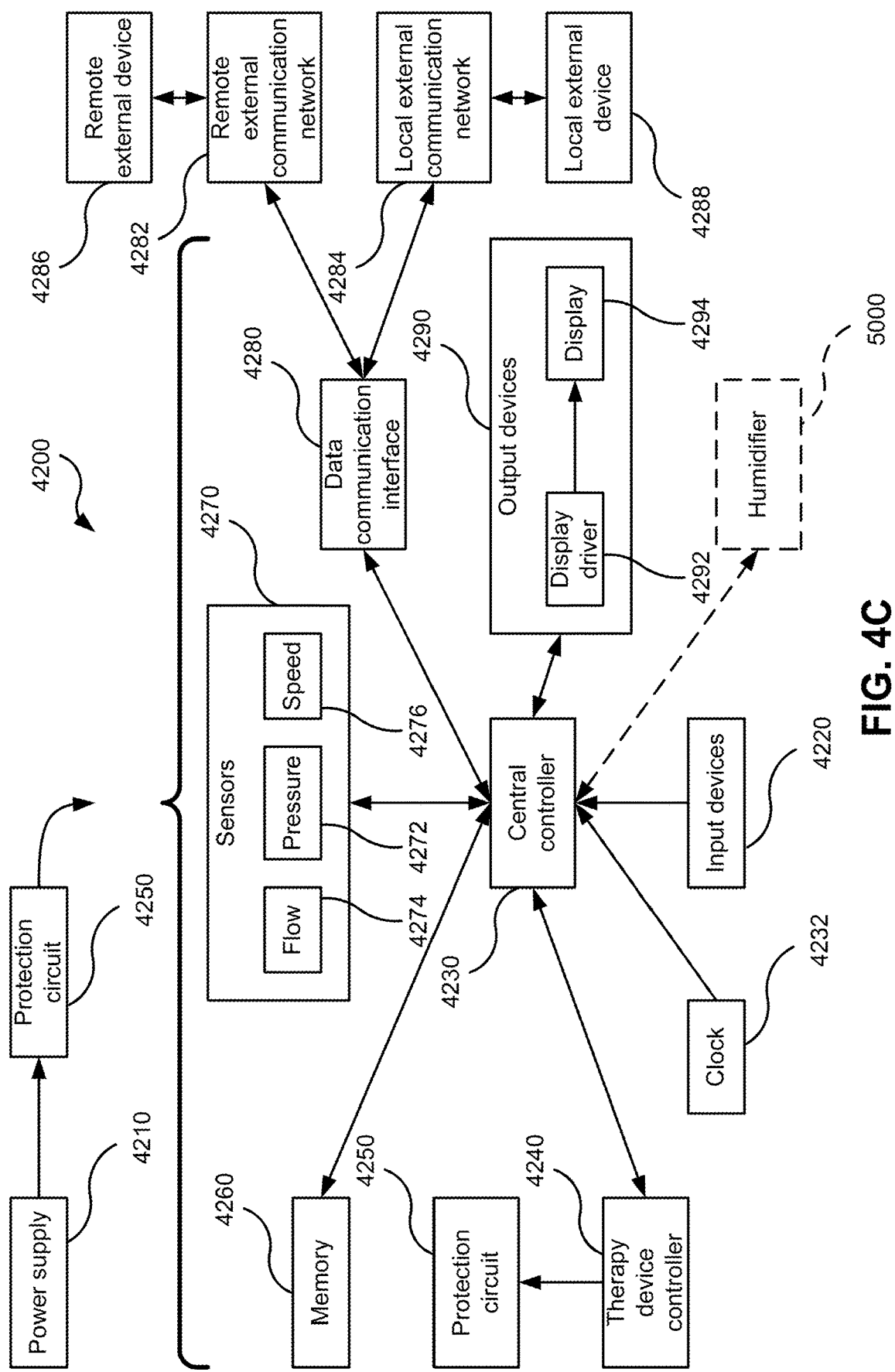

Upon interruption of the power provided by the electrical power supply 4210, components of the RPT device 4000 relying on the power supply 4210 stop operating. However, some components may need additional energy and time to shut down properly. As an example, the data communication interface 4280 (see FIG. 4C), performing wireless communication (e.g., cellular communication), may include components needing additional energy to properly shut down. Components including memory (e.g., non-volatile memory) may need additional energy to shut down properly after a power interruption. Without additional energy and time during the power interruption, data stored in the memory can be corrupted or fail to be stored during a program operation (e.g., writing to memory or erasing data in the memory).

One option is to include additional energy storage elements in the circuit to provide power upon interruption of the power from the power supply 4210. However, the additional energy storage elements increase cost and space needed on the printed circuit board.

Examples of the present technology, pass stored energy from a first circuit, which may have available energy in the event of power interruption, to a second circuit, which needs energy to properly shut down upon a power interruption. Sharing the stored energy between circuits upon power interruption allows for the number of redundant energy storage elements in the circuit to be reduced or completely eliminated, reducing cost and/or space needed by the circuit elements.

Figure 4D:
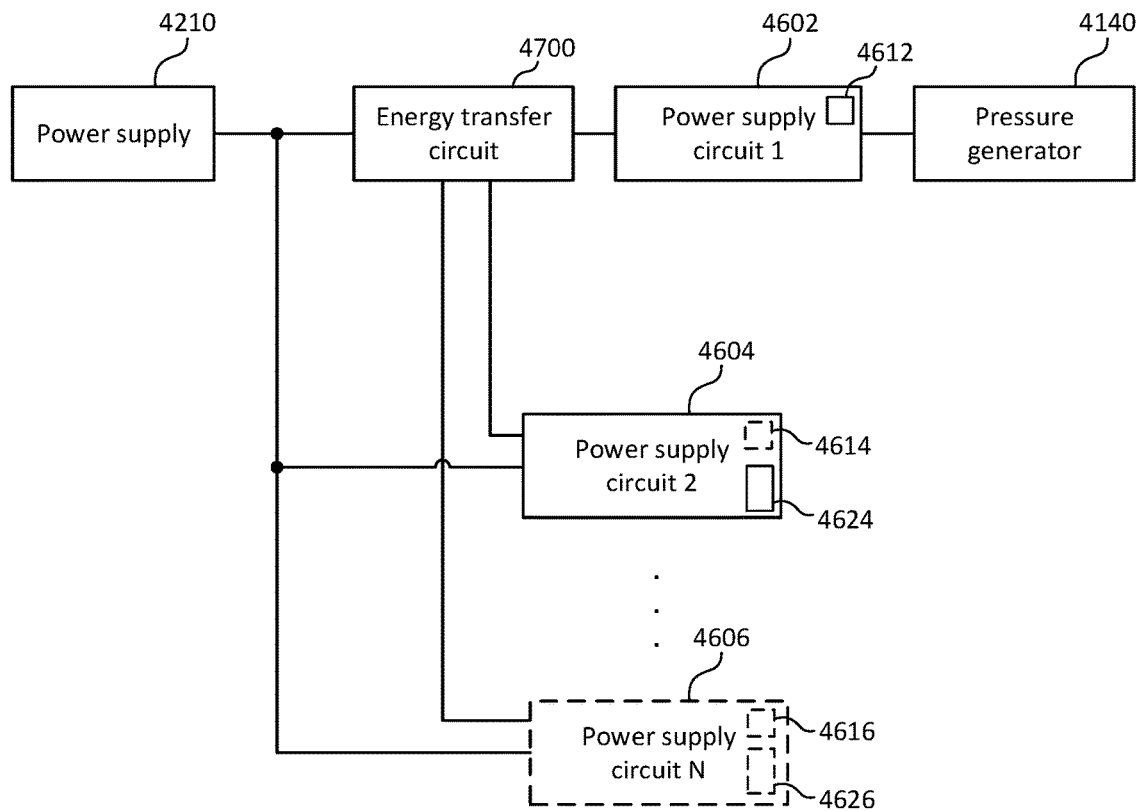

FIG. 4D shows a schematic diagram of electrical components configured to transfer energy upon power interruption in accordance with one form of the present technology. During operation, the power supply 4210 provides electrical power to a first power supply circuit 4602. The first power supply circuit 4602 may include any power circuit associated with the therapy device 4000, such as the motor 4144 power circuit. The power supply 4210 may also be configured to provide electrical power to a second power supply circuit 4604, as well as to one or more additional power supply circuits 4606. The second power supply circuit 4604 may, in one example, include the data communication interface 4280 performing wireless communication. An energy transfer circuit 4700 may also be introduced and configured to transfer power stored in the first power supply circuit 4602, to the second power supply circuit 4604, or to any one of the additional power supply circuits. The first or the second power supply circuit, or the energy transfer circuit 4700, may need to convert power and/or voltage received from the first power supply circuit 4602 to a level suitable for the operation of the components in the power receiving power supply circuit.

One example where energy stored in one circuit may need to be transferred to another circuit, is the case of a power interruption. After interruption of power provided by the power supply 4210, an energy transfer circuit 4700 may transfer energy stored in one or more energy storage elements 4612 of the first power supply circuit 4602 to the second power supply circuit 4604. The one or more energy storage elements 4612, which may include capacitors, are part of the circuit used during operation of the pressure generator 4140 while power is provided by the power supply 4210. The one or more energy storage elements 4612 may store energy provided by the power supply 4210 and provide the stored energy to the first power supply circuit 4602 at times of high peak demands. In addition, the system may be arranged so that, when the motor 4144 of the pressure generator 4140 is controlled to slow down, the regenerative power from the motor 4144 further charges the one or more energy storage elements 4612. The energy transfer circuit 4700 may transfer energy stored in one or more energy storage elements 4612 and energy generated by the deceleration of the motor.

The second power supply circuit 4604 can use the transferred energy to properly shut down one or more elements 4624 of the second power supply circuit 4604, such as in the event of a power interruption. The one or more elements 4624 may include memory, such as non-volatile memory.

In some examples, the voltage in the first power supply circuit 4602 may be different from the voltage used in the second power supply circuit 4604. The energy transfer circuit 4700 may be configured to convert the voltage from a first value provided by the one or more energy storage elements 4612 to a second value that is within the tolerance of the second power supply circuit 4604. In the process of reducing the voltage, the energy transfer circuit 4700 may dissipate some of the stored energy.

As shown in FIG. 4D, the RPT device 4000 may include one or more additional power supply circuits 4606 receiving power from the power supply 4210 during normal operation and receiving stored energy from the first power supply circuit 4602 upon interruption of power provided by the power supply 4210. The additional power supply circuit 4606 may similarly include one or more elements 4626 that need additional energy to properly shut down when the power is interrupted. The energy transfer circuit 4700 may provide the additional power supply circuits 4606 with a voltage that is similar to a voltage provided to the second power supply circuit 4604 or a voltage that is different to the voltage provided to the second power supply circuit 4604.

In some examples, the energy transfer circuit 4700 may be part of the first power supply circuit 4602.

While a pressure generator 4140 is shown in FIG. 4D, other devices providing regenerative power may be powered by the first power supply circuit 4602 and further charge the one or more energy storage elements 4612 when power from the power supply 4210 is interrupted.

Transferring the stored energy from the first power supply circuit 4602 to the one or more other power supply circuits upon power interruption, allows for energy storage elements 4614 in the second power supply circuit 4604 and/or energy storage elements 4616 in the additional power supply circuit 4606 to be reduced or removed, reducing cost and/or space needed by these circuit elements on the PCB.

The energy of the motor circuit (e.g., the first power supply circuit 4602) may have a higher voltage rating then the voltage rating of other circuits. As an example, the motor circuit may operation at higher voltages (e.g., up to 60V). Because of that, the motor circuit has traditionally been isolated from other circuits (e.g., device control and/or humidification circuits) which operate at lower voltages (e.g., 30-35V). However, examples of the present technology provide a transfer circuit that taps into the unused energy in the motor circuit and transfers the energy to other circuits needing the energy, i.e. to shut down properly.

Examples of the present technology provide access to extra energy with a small circuit, which saves both cost as well as Printed Circuit Board (PCB) real estate. Traditionally, to ensure enough energy during a power interruption, the second power supply circuit 4604 or circuitry outside of the second power supply circuit 4604 may include a plurality of storage elements 4614 storing energy for use during a power interruption. As an example, the second power supply circuit 4604 may include six 330 uF 35V capacitors storing energy for use during a power interruption. Reducing the number of these capacitors will reduce cost as well as PCB real estate because these capacitors are large in size.

The capacitors in the motor circuit may in some cases store more energy than is needed to be provided to the second power supply circuit 4604. As an example, the motor circuit may include two 330 μF capacitors. These are typically designed for a higher voltage and are, therefore, capable of storing more energy. However, as the voltage in the motor circuit may be higher than is the one used by the second power supply circuit 4604, the energy transfer circuit 4700 may need to reduce the voltage, before passing it onto the second power supply circuit 4604. During this voltage reduction some energy is dissipated before reaching the second power supply circuit 4604.

The energy transfer circuit 4700 needs to make sure that the voltage in the power supply circuit is safe (e.g., no more than 35V). Despite the dissipation losses, enough energy is passed on to shut down critical items, such as non-volatile memory in flash memory and cellular chip set (the 3G/4G connection chip)—allowing them to execute safely a shut-down routine. Accordingly, apart from its main energy transfer function, the energy transfer circuit 4700 has two further functions—a) it may need to bring the voltage down to safe level and b) it may dissipate some energy.

Figure 4E:
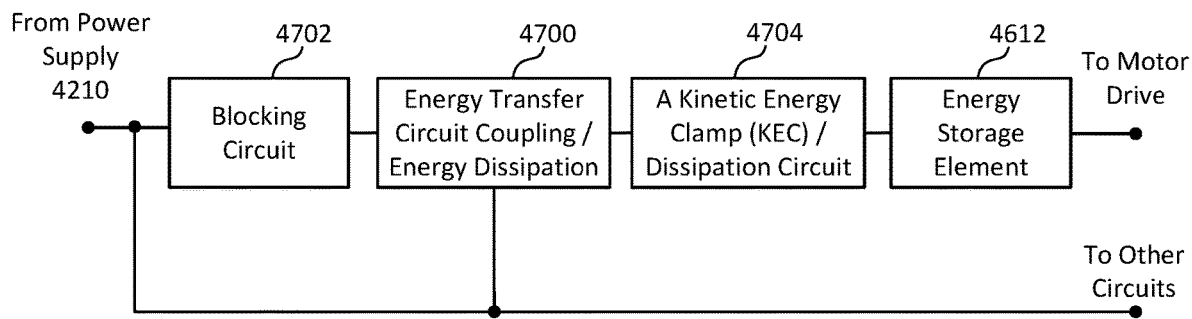

FIG. 4E shows a schematic diagram, including transfer circuit 4700, in accordance with one form of the present technology. In some instances, the illustrated circuits including the transfer circuit 4700, may also include any one or more of; a blocking circuit 4702, A Kinetic Energy Clamp (KEC) circuit 4704, and a storage element 4612. While the components of the transfer circuit 4700 are shown in a specific order in FIG. 4E, the order of the components is not so limited. For example, as the Kinetic energy clamp 4704 needs to control the voltage provided to the motor drive it may be provided in different locations of the circuit. For instance, diode 4710 in FIG. 4F starts conducting when the voltage across the diode gets above say 30V. In the case of controlled slowdown of the motor, the diode conducts enough current so that so as to maintain (clamp) the voltage at about 40V).

The power supply circuit illustrated in FIG. 4D allows energy from the power supply 4210 to pass to a motor driver to control a motor (e.g., the motor 4144 in the pressure generator 4140). The motor driver controls the motor to convert electrical energy into kinetic energy output by the motor. The motor driver controls operation of the motor, for example, using an H-Bridge based on setting of the RPT device 400 and signals received from one or more sensors 4270.

Figure 4F:
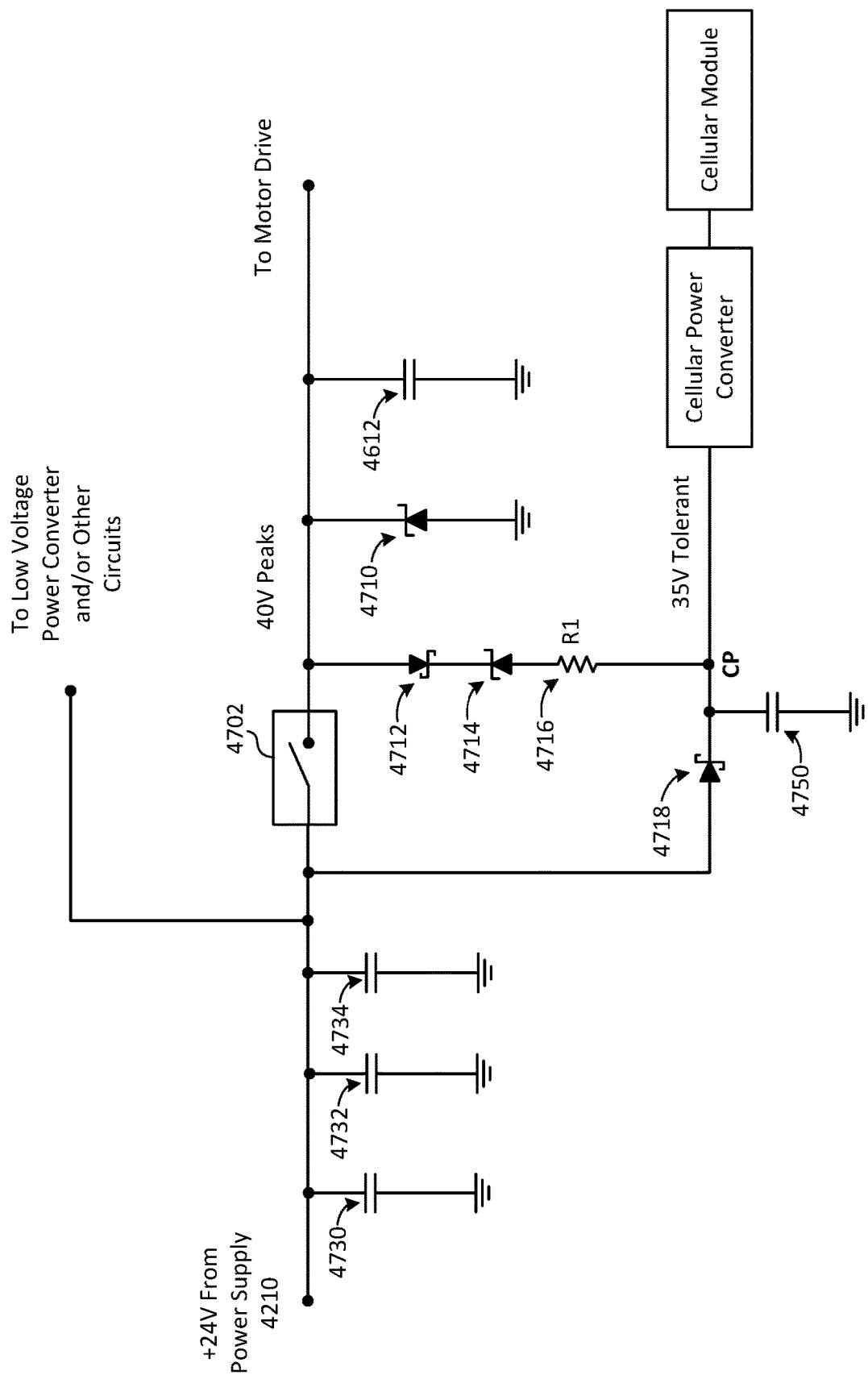

The storage elements 4612, may include one or more capacitors 4612, as shown in FIG. 4F. The one or more capacitors 4612 filter high energy peaks by buffering energy and providing it to the motor at time of high peak demand. Examples of the present technology allow for the storage elements 4612 to also provide energy to a different power system (e.g., not the motor power system, but the cellular power system), mostly upon shut down of the device.

The blocking circuit 4702 prevents energy and higher voltage, (i.e. generated by a decelerating motor) to flow to the power supply 4210, as the voltage generated by decelerating of the motor may exceed the voltage provided by the power supply 4210. The blocking circuit 4702 may include a blocking diode (e.g., a Schottky diode) or a switch (e.g., a transistor switch) configured to actuate when voltage generated by the deceleration of the motor exceeds voltage of the power supply 4210. A comparator or microcontroller (e.g. the central controller 4230 or on the therapy device controller 4240) may monitor the voltages and actuate the switch based on a comparison of the voltages. The kinetic energy clamp circuit 4704 may be configured to maintain the voltage passed onto one or more of the additional power supply circuits below a predetermined value. As an example, the kinetic energy clamp 4704 may shunt any voltage above 40 V in the case of increased voltage, i.e. during controlled motor deceleration. As during the operation of circuit 4704 there is usually energy dissipation, the circuit may also be referred to as an energy dissipation circuit. The circuit 4704 may include a diode (e.g., transistor-voltage suppression diode or a Zener diode—see diode 4710 in FIG. 4F) and/or a resistor(s). In some examples, the KEC/energy dissipation circuit 4704 may even include an active circuit configured to monitor voltage on the power rail (e.g., via a comparator) and control a switch to dissipate the energy when the voltage exceeds the predetermined value. Such a design is likely to be associated with a higher complexity and/or cost.

The energy transfer circuit 4700 may provide energy from storage element 4612 to another circuit, such as in case of a power interruption. The energy from the storage element 4612 can be used by the other circuit to properly close down elements (e.g., non-volatile memory which needs energy to shut down properly) and minimise memory corruption during power interruption.

In some examples of the present technology, the energy transfer circuit 4700 may be configured to pass energy from the first circuit to the second circuit when a voltage difference between a voltage on the first circuit power rail and a voltage on the second power rail exceeds a predetermined value. For example, the energy transfer circuit 4700 may be configured to pass energy between the circuits when the voltage difference between the motor driver power rail and the other circuit power rail exceeds 5 V. In this example, during normal operation both the motor driver power rail and the other circuit power rail would have same voltage levels (e.g., 24 V) and no energy will be transferred to the other circuit. However, during a power interruption, the voltage on the other circuit power rail will drop and the energy transfer circuit 4700 will be activated (due to the voltage difference) to start transferring energy from the storage elements to the other circuit power rail.

The energy transfer circuit 4700 may include a diode to conduct current for any voltage above a predetermined value. For example, the energy transfer circuit 4700 may include circuit elements (e.g., diodes and/or resistors) to ensure that the voltage transferred to the other power circuits is maintained at a substantially fixed value below the voltage of the motor drive, and/or that the voltage transferred to the other circuit does not exceed a tolerant value. The monitored parameter that triggers the power transfer may be either the voltage of the other circuit or the voltage difference between the voltages of the motor circuit and that of the other circuit.

In some example, as shown in FIG. 4F, the energy transfer circuit 4700 may include a first diode to prevent back current, a second diode to allow current to pass when voltage drop (between the voltage at 4612 and 4750) reaches a predetermined value, and a resistor to limit the current, connected in series between the power rail of the motor driver and the power rail of the other circuit.

In some examples, a plurality of coupling circuits may be coupled to the energy storage element 4612, with each energy transfer circuit providing energy upon power interruption to a different additional power supply circuit shown in FIGS. 4D and 4E. In this example, the voltage levels provided to each of the power supply circuit may be controlled by parameters of elements (e.g., a diode and/or a resistor) in the energy transfer circuit in a way similar to that described above.

FIG. 4F shows a schematic diagram including a circuit configured to transfer energy between power supply circuits in accordance with one form of the present technology. A power supply (i.e. power supply 4210) may provide power to multiple components coupled to the power supply. In FIG. 4F, 24V is provided to a 24V-rail, which is coupled to; a/ a low voltage power converter rail for powering one or more components (e.g., a low voltage power converter, a microcontroller and other circuits), b/ a motor driver power rail for powering a motor (e.g., the motor 4144 in the pressure generator 4140), and c/ a pre-cellular module power rail (labelled as CP rail), which feeds the cellular power converter that powers the cellular module. An active blocking circuit 4702, including one or more elements e.g., a diode circuit, is controlled by a microcontroller (such as the central controller 4230) and may couple and decouple the power supply 4210 to/from the motor power rail.

During operation, the blocking circuit 4702 allows energy from the power supply 4210 to flow to the motor driver for powering the motor and prevents regenerative energy flow from the motor driver to the power supply 4210 during controlled motor deceleration, i.e. when the motor driver controls the motor to decelerate. The blocking circuit 4702 may include a blocking diode or a transistor switch controlled by a circuit detecting deceleration of the motor, a motor power supply circuit and/or a microprocessor-based controller. When the energy from the motor deceleration causes the voltage on the motor rail to go above the power supply voltage (e.g., above 24 v), the active blocking diode circuit opens, preventing the higher voltage to reach the power supply 4210 and other circuits coupled to the power supply 4210.

The motor controller, not shown in FIG. 4F, can include a motor driver integrated circuit that is located on the motor power rail (to the right of the switch 4702) and drives power to the motor, as well as an associated software run on the central controller 4230 or on the therapy device controller 4240. When the motor controller signals to the motor to slow down, the system needs to limit the voltage to which the power storage element 4612 is charged, due to the regenerative energy introduced in the system by the motor deceleration. A Kinetic Energy Clamp (KEC) circuit includes diode 4710. When shunting any voltage above a pre-set first value (e.g., 40 V), diode 4710 also dissipates at least some of the incoming energy. A multi-diode KEC may also be implemented.

The energy transfer circuit discussed previously in the text, in this case includes diodes 4712 and 4714, and resistor R1 (4716). Diode 4714 conducts current for any voltage above a set value, which is the value of the voltage drop at the diode 4714 (i.e. approximately 5V), passing the voltage to another circuit (e.g., cellular power supply circuit). The operation of the diode 4714 ensures that a pre-set difference (i.e. 5V) is maintained between the Vmotor power rail and the CP rail. Resistor 4716 limits the current. Schottky Diode 4712 prevents back current from the CP rail.

A Schottky diode 4718 is provided on the CP rail to prevent higher voltage to go to the 24 v rail.

During normal operation conditions, the motor power rail and the CP rail have the same voltage, equal to the power supply voltage. Energy from the power supply 4210 is used to power the motor and charge the energy storage elements 4612 and 4750. These storage elements are used to filter the higher energy peaks, by buffering energy and providing it to the respective power rail at times of high peak demands. While a single storage capacitor is shown for each of these energy storage elements in FIG. 4F, the storage elements may include a plurality of capacitors provided in parallel and/or series to store energy.

During deceleration of the motor, the voltage on the motor rail may exceed the voltage provided by the power supply 4210 because of the regenerative power from the motor and further charge the storage element 4612. As discussed above, because the voltage on the power rail is clamped down by the diode 4710 (e.g., to 40V), the charge stored by the storage element 4612 will not exceed a pre-set value.

When the power is turned off, the voltage on the CP rail drops and, once the voltage drop below a predetermined value, CP rail gains access to power stored by the storage element 4612 via the path including the energy transfer circuit 4700 (diode 4714 and resistor 4716). The diode 4714 may only conduct current from the motor power rail to the CP rail when a voltage difference between the power rail to the CP rail exceeds a pre-set value. In one example, the diode 4714, which may be a zener diode, may conduct current for any voltage above 5V. Thus, the CP rail gains access to the power stored by the storage element 4612, with its voltage being approximately 5V smaller than that of the motor power supply rail. The storage element 4612 is charged at least to the voltage of the power supply 4210 (e.g., 24V) during operation of the motor and may be charged even higher (e.g., 40V) during motor deceleration.

The access to the power stored by the storage element 4612 can be used by the cellular power converter and/or cellular module to close down elements needing additional power after power interruption from the power supply 4210.

The power supply circuit may include access to other power sources. Such power sources may include, for example, one or more storage elements 4730, 4732, and 4734 (which may be 680 μF capacitors). However, the one or more storage elements 4730, 4732, and 4734 may not have sufficient power to ensure a proper shut down of various non-volatile memory that are part of the cellular circuit either. Such memories may include any one of EEPROM, flash RAM, and/or memory cards etc. needing additional power to shut down, so as to minimise memory corruption, if shut down improperly.

In some examples of the present technology, the number of storage elements 4730, 4732, and 4734 can be reduced because, as described above, power from the storage elements in the motor circuit can be provided during power interruption to the other circuits. With additional circuits and/or larger memory needing power to properly shut down when power is interrupted, it may be necessary to include both the storage elements 4730, 4732, and 4734, storage element 4750, as well as the above described energy transfer circuit 4700, to properly shut down the memories in the same circuit or multiple circuits.

Examples of the present technology includes providing access to the motor drive power circuit so as to provide spare energy to a system that may need to have access to additional energy, at the time of shut down, when the main energy source to this system is interrupted. This may be especially relevant in a tight space environment. Within the housing of an RPT device, a PCB comprising the circuitry according to examples of the present technology may need to be placed in very close proximity to other components, such as a case- or the pneumatic block—wall. Capacitors included in the storage elements 4730, 4732, and 4734 may have appreciable height. This could be a problem in the limited vertical design space often characterising RPT devices. In addition, these capacitors may unnecessary limit the PCB real estate, when they are in a larger number. The proposed energy transfer circuit including diode, 4712, diode 4714 and resistor 4716, can be made of low-profile components that are more suitable for the tight PCB design environment.

In some examples of the present technology, a storage element 4750 may optionally be included in the cellular power system. The storage element 4750 may include one or more capacitors. The primary usage of the storage element 4750 may include filtering pulsed current by buffering power and supplying at times of peak demand—thus reducing the voltage variation caused by the pulses form the cellular power circuit. The storage element 4750 may also serve as a spare power supply for the cellular power system during a power interruption, for example when the power stored in the storage elements 4730, 4732, and 4734 capacitors is exhausted.

When the energy transfer circuit transfers energy stored by the storage element 4612, the storage element 4750 may be charged further because the storage element 4750 voltage is lower (e.g., 5V lower) than voltage of the storage element 4612. In this example, the cellular power circuit gains access to the power of the storage element 4612 and/or further charges the storage element 4750 for closing down elements during power interruption.

Figure 4G:
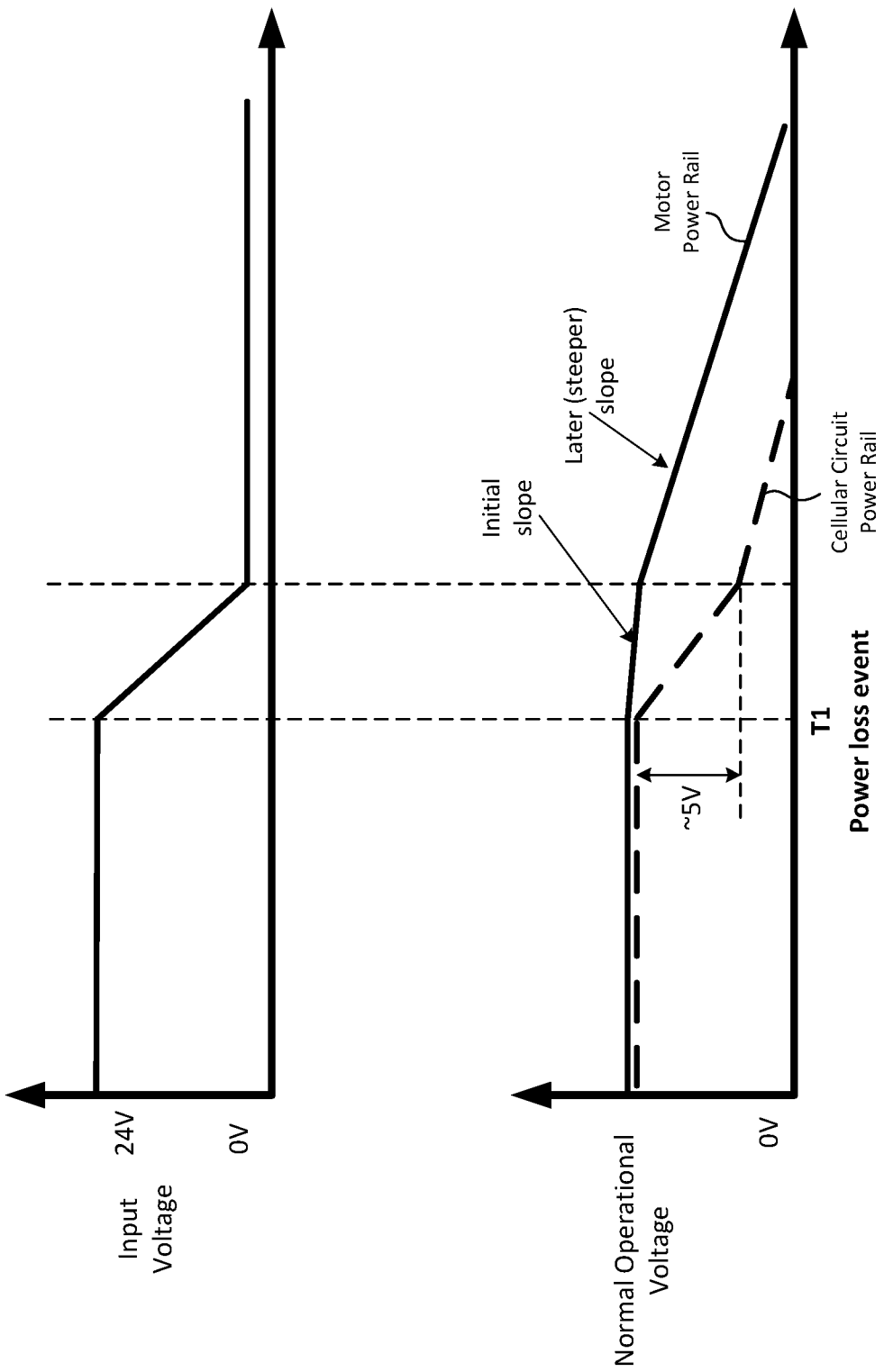

FIG. 4G shows graphs of exemplary voltage levels of circuitry configured to transfer energy between power supply circuits in accordance with one form of the present technology. A node coupled to an output of the power supply 4210 receives 24 volts during operation of the power supply 4210. When power from the power supply 4210 is interrupted at time T1, the voltage drops to zero volts on the power output node. The voltage may drop gradually if one or more capacitors (e.g., storage elements 4730, 4732, 4734) are included in the 24V power supply rail.

While power is provided to the motor from the power supply 4210, the motor power rail receives 24 volts. When power is interrupted, the voltage starts decreasing and slowly diminishes to zero (see the top graph of the bottom figure).

Before power interruption, the cellular circuit power rail receives 24 volts from the power supply 4210. When power is interrupted, the voltage on the cellular circuit power rail decreases. The voltage may decrease gradually if the cellular circuit power rail receives stored charge from one or more capacitors (e.g., storage elements 4750, as well as possibly 4730, 4732, 4734) coupled to the output node of the power supply.

When the voltage drop between the motor drive rail and the cellular power rail reaches a predetermine difference (say about 5V), the cellular circuit power rail gains access to energy on the motor power rail (e.g., energy stored in the storage elements). The access to the energy on the motor power rail causes the decrease in the voltage on the cellular circuit power rail to slow down, by now following a different slope. The new slope is less steep than that of the initial voltage drop (before having access to the motor drive power rail), but steeper than the voltage reduction in the motor drive rail itself. Thus, the cellular circuit power rail may continue for a bit longer to receive power which is within the operating tolerance of the cellular circuit, allowing for non-volatile memory to close down properly.

In one form of the present technology, the energy transfer circuit 4700 is so designed that, even if no further energy is gained during the deceleration of the motor, the access provided to the communication power supply circuit, or any other circuit, to the energy stored in the power supply circuit of the motor, allows these other circuits to safely execute any necessary shut down routines. This is at least partially facilitated by the fact that the other power supply circuits may have a lower operational voltage (i.e. 35V and lower— up to about 6V) than the motor drive circuit (i.e. 40V)

In one form of the present technology, the cellular circuit may receive regenerative power from the motor deceleration during normal operation while the power supply is operating and providing power to cellular circuit.

It should be noted that whilst the above text described various components of the power supply circuit for an RPT device, such as KEC/energy dissipation circuit 4704, storage element 4612, blocking circuit 4702 etc., these were described mostly as a context of the main focus of this technology—the energy transfer circuit 4700. Whilst in one form this energy transfer circuit was described as including elements 4712, 4714 and 4716, alternative circuits that fulfil the same functions (energy transfer function, voltage limiting function and back current prevention) may also be use within the scope of this technology. Whist the first two functions a compulsory, the third one is optional and in some cases may be omitted. In one alternative example, a voltage regulator may be used to transfer a reduced voltage to between the two power supply rails. However, this is an expensive solution that is generally directed to solving different problems (maintaining a fixed output voltage). The above described solution is much simpler and less expensive practical solution.

As used in any of the examples in the present technology, "circuitry" may comprise, for example, singly or in any combination, analog circuitry, digital circuitry, hardwired circuitry, programmable circuitry, state machine circuitry, and/or firmware that stores instructions executed by programmable circuitry. Also, in any example herein, circuitry may be embodied as, and/or form part of, one or more integrated circuits.

4.5 Air Circuit

An air circuit 4170 in accordance with an aspect of the present technology is a conduit or a tube constructed and arranged to allow, in use, a flow of air to travel between two components such as RPT device 4000 and the patient interface 3000.

In particular, the air circuit 4170 may be in fluid connection with the outlet of the pneumatic block 4020 and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller 4230. One example of an air circuit 4170 comprising a heated wire circuit is described in U.S. Pat. No. 8,733,349, which is incorporated herewithin in its entirety by reference.

4.5.1 Supplementary Gas Delivery

In one form of the present technology, supplementary gas, e.g. oxygen, 4180 is delivered to one or more points in the pneumatic path, such as upstream of the pneumatic block 4020, to the air circuit 4170, and/or to the patient interface 3000.

4.6 Humidifier

4.6.1 Humidifier Overview

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

In one form, the humidifier 5000 may comprise a humidifier reservoir dock 5130 (as shown in FIG. 5B) configured to receive the humidifier reservoir 5110. In some arrangements, the humidifier reservoir dock 5130 may comprise a locking feature such as a locking lever 5135 configured to retain the reservoir 5110 in the humidifier reservoir dock 5130. The humidifier reservoir 5110 may comprise a water level indicator 5150 as shown in FIG. 5A-5B.

4.6.2 CPAP Therapy

In some implementations of respiratory pressure therapy, the central controller 4230 sets the treatment pressure Pt according to the treatment pressure equation (Error! Reference source not found.) as part of the therapy parameter determination algorithm. In one such implementation, the amplitude A is identically zero, so the treatment pressure Pt (which represents a target value to be achieved by the interface pressure Pm at the current instant of time) is identically equal to the base pressure $P_0$ throughout the respiratory cycle. Such implementations are generally grouped under the heading of CPAP therapy. In such implementations, there is no need for a therapy engine module to determine phase Φ or the waveform template Π(Φ).

In CPAP therapy, the base pressure $P_0$ may be a constant value that is hard-coded or manually entered to the RPT device 4000. Alternatively, the central controller 4230 may repeatedly compute the base pressure $P_0$ as a function of indices or measures of sleep disordered breathing returned by the respective algorithms in the therapy engine module, such as one or more of flow limitation, apnea, hypopnea, patency, and snore. This alternative is sometimes referred to as APAP therapy.

4.6.3 Bi-Level Therapy

In other implementations of this form of the present technology, the value of amplitude A in equation (Error! Reference source not found.) may be positive. Such implementations are known as bi-level therapy, because in determining the treatment pressure Pt using equation (Error! Reference source not found.) with positive amplitude A, the therapy parameter determination algorithm oscillates the treatment pressure Pt between two values or levels in synchrony with the spontaneous respiratory effort of the patient 1000. That is, based on the typical waveform templates $\Pi(\Phi, t)$ described above, the therapy parameter determination algorithm increases the treatment pressure Pt to $P_0+A$ (known as the IPAP) at the start of, or during, or inspiration and decreases the treatment pressure Pt to the base pressure $P_0$ (known as the EPAP) at the start of, or during, expiration.

4.7 Glossary

For the purposes of the present technology disclosure, in certain forms of the present technology, one or more of the following definitions may apply. In other forms of the present technology, alternative definitions may apply.

4.7.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Device flow rate, Qd, is the flow rate of air leaving the RPT device. Total flow rate, Qt, is the flow rate of air and any supplementary gas reaching the patient interface via the air circuit. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Flow therapy: Respiratory therapy comprising the delivery of a flow of air to an entrance to the airways at a controlled flow rate referred to as the treatment flow rate that is typically positive throughout the patient's breathing cycle.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Patient: A person, whether or not they are suffering from a respiratory condition.

Pressure: Force per unit area. Pressure may be expressed in a range of units, including $cmH_2O$, $g-f/cm^2$ and hectopascal. 1 $cmH_2O$ is equal to 1 $g-f/cm^2$ and is approximately 0.98 hectopascal (1 hectopascal=100 Pa=100 N/m2=1 millibar~0.001 atm). In this specification, unless otherwise stated, pressure is given in units of $cmH_2O$.

The pressure in the patient interface is given the symbol Pm, while the treatment pressure, which represents a target value to be achieved by the interface pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

4.7.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a thermoplastic polymer of Bisphenol-A Carbonate.

4.7.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

- 'Soft' materials may include silicone or thermo-plastic elastomer (TPE), and may, e.g. readily deform under finger pressure.
- 'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions. The inverse of stiffness is flexibility.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 cmH$_2$O pressure.

As an example, an I-beam may comprise a different bending stiffness (resistance to a bending load) in a first direction in comparison to a second, orthogonal direction. In another example, a structure or component may be floppy in a first direction and rigid in a second direction.

4.7.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:
(i) Flattened: Having a rise followed by a relatively flat portion, followed by a fall.
(ii) M-shaped: Having two local peaks, one at the leading edge, and one at the trailing edge, and a relatively flat portion between the two peaks.
(iii) Chair-shaped: Having a single local peak, the peak being at the leading edge, followed by a relatively flat portion.
(iv) Reverse-chair shaped: Having a relatively flat portion followed by single local peak, the peak being at the trailing edge.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:
(i) a 30% reduction in patient breathing for at least 10 seconds plus an associated 4% desaturation; or
(ii) a reduction in patient breathing (but less than 50%) for at least 10 seconds, with an associated desaturation of at least 3% or an arousal.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peakflow rate (Qpeak): The maximum value of flow rate during the inspiratory portion of the respiratory flow waveform.

Respiratory flow rate, patient airflow rate, respiratory airflow rate (Qr): These terms may be understood to refer to the RPT device's estimate of respiratory flow rate, as opposed to "true respiratory flow rate" or "true respiratory flow rate", which is the actual respiratory flow rate experienced by the patient, usually expressed in litres per minute.

Tidal volume (Vt): The volume of air inhaled or exhaled during normal breathing, when extra effort is not applied. In principle the inspiratory volume Vi (the volume of air inhaled) is equal to the expiratory volume Ve (the volume of air exhaled), and therefore a single tidal volume Vt may be defined as equal to either quantity. In practice the tidal volume Vt is estimated as some combination, e.g. the mean, of the inspiratory volume Vi and the expiratory volume Ve.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of one inspiratory portion of a respiratory flow rate waveform and the start of the following inspiratory portion of the respiratory flow rate waveform.

Typical recent ventilation: The value of ventilation around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

4.7.3 Ventilation

Adaptive Servo-Ventilator (ASV): A servo-ventilator that has a changeable, rather than fixed target ventilation. The changeable target ventilation may be learned from some characteristic of the patient, for example, a respiratory characteristic of the patient.

Backup rate: A parameter of a ventilator that establishes the minimum breathing rate (typically in number of breaths per minute) that the ventilator will deliver to the patient, if not triggered by spontaneous respiratory effort.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

Expiratory positive airway pressure (EPAP): a base pressure, to which a pressure varying within the breath is added to produce the desired interface pressure which the ventilator will attempt to achieve at a given time.

End expiratory pressure (EEP): Desired interface pressure which the ventilator will attempt to achieve at the end of the expiratory portion of the breath. If the pressure waveform template $\Pi(\Phi)$ is zero-valued at the end of expiration, i.e. $\Pi(\Phi)=0$ when $\Phi=1$, the EEP is equal to the EPAP.

Inspiratory positive airway pressure (IPAP): Maximum desired interface pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the base pressure (e.g., PS=IPAP−EPAP). In some contexts pressure support means the difference which the ventilator aims to achieve, rather than what it actually achieves.

Servo-ventilator: A ventilator that measures patient ventilation, has a target ventilation, and which adjusts the level of pressure support to bring the patient ventilation towards the target ventilation.

Spontaneous/Timed (S/T): A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator delivers a breath of air to a spontaneously breathing patient, it is said to be triggered to do so at the initiation of the respiratory portion of the breathing cycle by the patient's efforts.

4.8 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

| 4.9 REFERENCE SIGNS LIST | |
|---|---|
| patient | 1000 |
| bed partner | 1100 |
| patient interface | 3000 |
| seal-forming structure | 3100 |
| plenum chamber | 3200 |
| structure | 3300 |
| vent | 3400 |
| connection port | 3600 |
| forehead support | 3700 |
| ISO | 3744 |
| RPT device | 4000 |
| external housing | 4010 |
| upper portion | 4012 |
| portion | 4014 |
| panels | 4015 |
| chassis | 4016 |
| handle | 4018 |
| pneumatic block | 4020 |
| air filter | 4110 |
| inlet air filter | 4112 |
| outlet air filter | 4114 |
| muffler | 4120 |
| inlet muffler | 4122 |
| outlet muffler | 4124 |
| pressure generator | 4140 |

-continued

| 4.9 REFERENCE SIGNS LIST | |
|---|---|
| blower | 4142 |
| motor | 4144 |
| brushless DC motor | 4144 |
| anti-spill back valve | 4160 |
| air delivery tube | 4170 |
| air circuit | 4170 |
| heating air circuit | 4171 |
| supplementary gas | 4180 |
| electrical components | 4200 |
| PCBA | 4202 |
| power supply | 4210 |
| input device | 4220 |
| central controller | 4230 |
| clock | 4232 |
| therapy device controller | 4240 |
| protection circuits | 4250 |
| memory | 4260 |
| transducer | 4270 |
| pressure sensor | 4272 |
| flow rate sensor | 4274 |
| motor speed transducer | 4276 |
| data communication interface | 4280 |
| remote external communication network | 4282 |
| local external communication network | 4284 |
| remote external device | 4286 |
| local external device | 4288 |
| output device | 4290 |
| display driver | 4292 |
| display | 4294 |
| first power supply circuit | 4602 |
| second power supply circuit | 4604 |
| additional power supply circuit | 4606 |
| storage element | 4612 |
| storage elements | 4614 |
| storage elements | 4616 |
| elements | 4624 |
| elements | 4626 |
| transfer circuit | 4700 |
| blocking circuit | 4702 |
| KEC/energy dissipation circuit | 4704 |
| diode | 4710 |
| diode | 4712 |
| diode | 4714 |
| resistor | 4716 |
| schottky diode | 4718 |
| storage element | 4730 |
| storage element | 4732 |
| storage element | 4734 |
| storage element | 4750 |
| humidifier | 5000 |
| humidifier inlet | 5002 |
| humidifier outlet | 5004 |
| humidifier base | 5006 |
| reservoir | 5110 |
| conductive portion | 5120 |
| humidifier reservoir dock | 5130 |
| locking lever | 5135 |
| water level indicator | 5150 |
| heating element | 5240 |

The invention claimed is:

1. An apparatus for treating a respiratory disorder in a patient, the apparatus comprising:
a power supply node configured to be coupled to a power supply;
a pressure generator including a motor, the pressure generator configured to generate a flow of air for treating the respiratory disorder;
a motor power supply circuit coupled to the power supply node and the pressure generator; and
a first other power supply circuit;
wherein the motor power supply circuit includes:
one or more storage elements coupled to the motor and the power supply node, the one or more storage elements configured to store energy supplied by the power supply, and provide stored energy to the motor during operation of the motor; and an energy transfer circuit configured to couple the one or more storage elements to the first other power supply circuit and transfer energy stored by the one or more storage elements to the first other power supply circuit, in the case of power interruption.

2. The apparatus of claim 1, wherein the energy transfer circuit is arranged to transfer power from the one or more storage elements to the first other power supply circuit, only when a voltage difference between a voltage associated with the one or more storage elements, and a voltage associated with the first other power supply circuit, exceeds a predetermined value.

3. The apparatus of claim 2, wherein the one or more storage elements are configured to store energy generated by deceleration of the motor.

4. The apparatus of claim 1, wherein the motor power supply circuit operates at higher voltage than the first other power supply circuit.

5. The apparatus of claim 1, wherein the energy transfer circuit is configured to transfer power to the first other power supply circuit such that the transferred power has a lower voltage than a voltage of the motor power supply circuit.

6. The apparatus of claim 1, wherein the motor power supply circuit includes a blocking circuit configured to block transfer of energy to the power supply node.

7. The apparatus of claim 1, wherein the energy transfer circuit includes a first diode, a second diode and a resistor connected in series, the first diode is configured to block current flow from the first other power supply circuit to the motor power supply circuit, the second diode is configured to allow current to pass from the one or more storage elements to the first other power supply circuit when a voltage difference between a voltage on the one or more storage elements and a power rail of the first other power supply circuit exceeds a predetermined value, and the resistor is configured to limit current flow from the motor power supply circuit to the first other power supply circuit, a voltage drop over the second diode ensuring a constant offset between a voltage of the first other power supply circuit and that of the one or more storage elements.

8. The apparatus of claim 1, wherein the motor power supply circuit further includes:
an energy dissipation circuit, and
an active blocking diode circuit disposed on a motor power rail configured to block current flow from the motor power rail to the power supply node.

9. The apparatus of claim 1, wherein the first other power supply circuit includes non-volatile memory.

10. The apparatus of claim 1, wherein the first other power supply circuit includes a cellular circuit including memory.

11. The apparatus of claim 1, wherein the first other power supply circuit uses the transfer energy to shut down non-volatile memory during interruption of power provided by the power supply.

12. The apparatus of claim 1, wherein a motor drive circuit is configured to, during controlled motor deceleration, pass energy generated by deceleration of the motor to the one or more storage elements and/or an energy dissipation circuit.

13. The apparatus of claim 1, further comprising one or more capacitors coupled to the power supply node, the motor power supply circuit, and the first other power supply circuit.

14. The apparatus of claim 1, wherein the first other power supply circuit includes a cellular power circuit coupled to the power supply node, via a Schottky diode and a coupling circuit, the cellular power circuit configured to supply power to a cellular circuit including memory.

15. The apparatus of claim 1, further comprising a transducer configured to generate a flow signal representing a property of the flow of air, and a motor controller configured to control operation of the motor based on the flow signal.

16. The apparatus of claim 1, wherein the one or more storage elements are configured to store energy generated by deceleration of the motor.

17. The apparatus of claim 1, wherein the motor power supply circuit further includes an energy dissipation circuit coupled to the motor and configured to dissipate energy generated by deceleration of the motor.

18. The apparatus of claim 1, further comprising the power supply and wherein the power supply is a battery.

19. The apparatus of claim 1, wherein the power supply is an alternating current power supply or a direct current power supply disposed external to a housing of the apparatus.

20. An apparatus for providing positive pressure respiratory therapy to a patient breathing in a respiratory cycle including an inhalation portion and an exhalation portion, said apparatus comprising:
a power supply node configured to be coupled to a power supply;
a first power supply circuit coupled to the power supply node;
a controllable motor-blower configured to generate a supply of air at a positive pressure relative to ambient pressure by rotating an impeller at an impeller speed,
a housing holding said motor-blower, the housing comprising an inlet and a patient-connection port, the patient-connection port being structured to communicate said supply air at said positive pressure from the motor-blower to a patient interface via an air circuit in use;
a sensor to monitor at least one of pressure and a flow rate of the supply of air at positive pressure and to generate a sensor output; and
a motor controller coupled to the power supply node and configured to adjust an operating parameter of said motor-blower in accordance with said sensor output to maintain a minimum positive pressure in said patient interface during a treatment session by causing an increase in the impeller speed during the inhalation portion of the respiratory cycle and causing a decrease in the impeller speed during the exhalation portion of the breathing cycle; and
power circuitry configured and controlled to enable:
storage of energy generated by deceleration of the motor-blower in one or more storage elements;
dissipation of a portion of the energy generated by the deceleration of the motor-blower;
transfer of energy generated by the deceleration of the motor-blower and/or the energy stored in the one or more storage elements, to the first power supply circuit; and
blocking of current flowing from a motor power rail to the power supply node.

21. The apparatus of claim 20, wherein the first power supply circuit includes a cellular power circuit configured to supply power to a cellular circuit including memory.

22. The apparatus of claim 20, wherein the first power supply circuit includes non-volatile memory.

23. The apparatus of claim 20, wherein the power circuitry includes a first diode, a second diode and a resistor connected in series between a power rail of the motor controller and the first power supply circuit, the first diode is configured to block current flow from the first power supply circuit to the motor controller, the second diode is configured to pass the energy generated by the deceleration of the motor-blower and the stored energy to the first power supply circuit when a voltage difference between a voltage on the power rail of the motor controller and a voltage of the first power supply circuit exceeds a predetermined value, and the resistor is configured to limit current flow to the first power supply circuit.

24. The apparatus of claim 20, wherein the power circuitry is configured to transfer the energy generated by the deceleration of the motor-blower and the stored energy to the first power supply circuit upon interruption of power provided by the power supply.

25. The apparatus of claim 20, further comprising the power supply and wherein the power supply is a battery.

26. The apparatus of claim 20, wherein the power supply is an alternating current power supply or a direct current power supply disposed external to a housing of the apparatus.

27. An apparatus for treating a respiratory disorder in a patient, the apparatus comprising:
 a power supply node configured to be coupled to a power supply;
 a cellular communication power supply circuit coupled to the power supply node;
 a pressure generator including a motor, the pressure generator configured to generate a flow of air for treating the respiratory disorder;
 a transducer configured to generate a flow signal representing a property of the flow of air;
 motor power supply circuitry coupled to the power supply node and the pressure generator, the motor power supply circuitry including:
  a motor power rail coupling the power supply node to the motor;
  a motor controller coupled to the motor power rail and configured to control supply of power to the motor based on the flow signal;
  an active blocking diode circuit disposed on the motor power rail and controlled to block transfer energy from the motor power rail to the power supply node;
  one or more capacitors coupled to the motor power rail and configured to store energy supplied by the power supply, provide the stored energy to the motor during operation of the motor, and store energy generated by deceleration of the motor;
  a kinetic energy clamp circuit coupled to the motor power rail and configured to dissipate energy generated by the deceleration of the motor that is above a predetermined first voltage level; and
  a transfer circuit including a first diode, a second diode and a resistor coupled in series between the motor power rail and the cellular communication power supply circuit, the first diode configured to block current flow from the cellular communication power supply circuit to the motor power rail, the second diode configured to allow current to pass from the one or more capacitors to the cellular communication power supply circuit when a voltage difference between a voltage on the motor power rail and a voltage of a pre-cellular module power rail exceeds a predetermined second voltage level, and the resistor configured to limit current flow from the motor power rail to the cellular communication power supply circuit.

28. The apparatus of claim 27, wherein the cellular communication power supply circuit includes a power converter and memory.

29. The apparatus of claim 27, wherein the cellular communication power supply circuit includes non-volatile memory.

30. The apparatus of claim 27, wherein the voltage difference between the voltage on the motor power rail and the voltage of the pre-cellular module power rail exceeds the predetermined second voltage level upon interruption of power provided by the power supply.

31. The apparatus of claim 27, further comprising the power supply and wherein the power supply is a battery.

32. The apparatus of claim 27, wherein the power supply is an alternating current power supply or a direct current power supply disposed external to a housing of the apparatus.

* * * * *